(12) United States Patent
Otsuki et al.

(10) Patent No.: US 11,521,511 B2
(45) Date of Patent: Dec. 6, 2022

(54) PROCESSING SYSTEM, WALKING TRAINING SYSTEM, PROCESSING METHOD, AND PROGRAM

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP); Natsuki Yamakami, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 299 days.

(21) Appl. No.: 16/876,236

(22) Filed: May 18, 2020

(65) Prior Publication Data
US 2020/0410892 A1    Dec. 31, 2020

(30) Foreign Application Priority Data

Jun. 28, 2019  (JP) .............................. JP2019-121891

(51) Int. Cl.
*G09B 19/00*     (2006.01)
*G06V 40/20*     (2022.01)
(Continued)

(52) U.S. Cl.
CPC .......... *G09B 19/003* (2013.01); *G06V 40/25* (2022.01); *A61H 1/024* (2013.01); *A61H 3/008* (2013.01); *A63B 22/02* (2013.01)

(58) Field of Classification Search
CPC . A61B 2505/09; A61B 2560/00; A61B 5/103; G09B 19/003; A61H 3/008;
(Continued)

(56) References Cited

U.S. PATENT DOCUMENTS

| 9,974,478 | B1* | 5/2018 | Brokaw | A61B 5/486 |
| 2014/0276130 | A1* | 9/2014 | Mirelman | A61B 5/112 |
| | | | | 600/595 |

(Continued)

FOREIGN PATENT DOCUMENTS

| CN | 104826230 A | 8/2015 |
| CN | 107469295 A | 12/2017 |

(Continued)

*Primary Examiner* — Omkar A Deodhar
(74) *Attorney, Agent, or Firm* — Oliff PLC

(57) ABSTRACT

A processing system capable of educating a training assistant, who assists a trainee when the trainee performs rehabilitation by using a walking training apparatus, in order to enable the training assistant to appropriately assist the trainee is provided. The processing system includes a determination unit and an output unit. The determination unit determines an adjustment-required parameter, the adjustment-required parameter being, among parameters that can be adjusted in a walking training apparatus, a parameter of which a frequency of adjustments by a training assistant who assists a trainee performing walking training in the walking training apparatus or by an assistant in a hospital other than the training assistant is lower than an adjustment criterion. The output unit outputs parameter information indicating the adjustment-required parameter and effect information indicating an adjustment effect that is obtained when the adjustment-required parameter is adjusted.

14 Claims, 9 Drawing Sheets

(51) Int. Cl.
  *A61H 1/02* (2006.01)
  *A61H 3/00* (2006.01)
  *A63B 22/02* (2006.01)

(58) Field of Classification Search
  CPC .... A61H 1/0262; A61H 1/024; A61H 1/0229; A61H 1/0237; A61H 3/00; G06K 9/00348; A63B 21/00181; A63B 21/4011; A63B 22/02; A63B 22/0235
  See application file for complete search history.

(56) References Cited

U.S. PATENT DOCUMENTS

| | | | |
|---|---|---|---|
| 2015/0217112 | A1 | 8/2015 | Shimoda et al. |
| 2015/0342820 | A1 | 12/2015 | Shimada et al. |
| 2018/0369053 | A1* | 12/2018 | Lukashevich ........ A61H 1/0262 |
| 2019/0105217 | A1* | 4/2019 | Prattichizzo ......... A61B 5/6828 |
| 2019/0160337 | A1 | 5/2019 | Otsuki et al. |

FOREIGN PATENT DOCUMENTS

| | | | |
|---|---|---|---|
| CN | 109701208 | A | 5/2019 |
| CN | 109846677 | A | 6/2019 |
| EP | 3489961 | A1 | 5/2019 |
| JP | 6052234 | B2 | 12/2016 |

* cited by examiner

| ADJUSTMENT-REQUIRED PARAMETER | ADJUSTMENT METHOD | EFFECT OF ADJUSTMENT |
|---|---|---|
| ANKLE JOINT DORSIFLEXION LIMITATION | TO DORSIFLEXION SIDE | TOE-OFF BECOMES EASIER |
| SWINGING ASSISTANCE LEVEL | UP | WALKING GENERALLY BECOMES EASIER |
| TREADMILL SPEED | DOWN | TO FORWARD-BENDING POSTURE |
| SWINGING FORWARD/BACKWARD RATIO | FORWARD | |
| WEIGHT-OFF THRESHOLD | DOWN | SWINGING ASSISTANCE TIME IS INCREASED |
| LOAD THRESHOLD | DOWN | |
| WEDGE THICKNESS | INCREASE | TOE-OFF BECOMES EASIER |

Fig. 8

PROCESSING SYSTEM, WALKING TRAINING SYSTEM, PROCESSING METHOD, AND PROGRAM

CROSS REFERENCE TO RELATED APPLICATIONS

This application is based upon and claims the benefit of priority from Japanese patent application No. 2019-121891, filed on Jun. 28, 2019, the disclosure of which is incorporated herein in its entirety by reference.

BACKGROUND

The present disclosure relates to a processing system, a walking training system, a processing method, and a program.

Trainees such as patients may use a rehabilitation support system such as a walking training apparatus when they perform rehabilitation. As an example of the walking training apparatus, Japanese Patent No. 6052234 discloses a walking training apparatus including a walking assistance apparatus that is attached to a leg of a trainee and assists the trainee in walking.

In some rehabilitation support systems, when a trainee performs rehabilitation, a training staff member such as a doctor or a physical therapist may attend the rehabilitation as an assistant for the trainee, give encouraging talks to the trainee, give a helping hand to the trainee, and/or perform a setting operation for the rehabilitation support system.

SUMMARY

Incidentally, in order to obtain good training results, the setting operation of the rehabilitation support system performed by the training staff member needs to be performed so that the rehabilitation support system can appropriately assist the trainee. Further, the timing of the setting operation, i.e., the timing at which assistance is added or ceased, or at which the degree of assistance is changed also affects the training results. Therefore, in order to perform such a setting operation, the training staff member needs to make a choice as to what kind of assistance should be given to the trainee, and determine an appropriate degree of the assistance and its timing. Further, the training staff member needs to determine what kind of encouraging talks he/she should give to the trainee and when he/she should give such talks to the trainee, and determine the timing at which he/she should give a helping hand to the trainee.

However, in the present circumstances, the training staff member makes the above-described determinations by intuition and/or knack. Further, since the years of experience and the level of proficiency vary among the training staff members, the difference in training results among the training staff members becomes considerably large. In particular, in the case of the waking training apparatus, it is difficult to make the above-described determination and hence the differences among training results of training staff members become considerably large. Therefore, it is desirable to educate training staff members so that the above-described differences are reduced and even training staff members who do not have sufficient years of experience and a sufficient level of proficiency can provide satisfactory training results. To that end, there is need for a technique capable of efficiently and appropriately educate training staff members of the walking training apparatus. Further, the assistance to the trainee is not limited to those given by the training staff members. That is, it is conceivable that assistance may be given by other kinds of training assistants such as artificial assistants. Therefore, it is desirable to efficiently and appropriately educate other kinds of training assistants.

The present disclosure has been made in order to solve the above-described problem and provides a processing system and the like capable of educating a training assistant, who assists a trainee when the trainee performs rehabilitation by using a walking training apparatus, so that the training assistant can appropriately assist the trainee.

A first exemplary aspect is a processing system including: a determination unit configured to determine an adjustment-required parameter, the adjustment-required parameter being, among parameters that can be adjusted in a walking training apparatus, a parameter of which a frequency of adjustments by a training assistant who assists a trainee performing walking training in the walking training apparatus or by an assistant in a hospital other than the training assistant is lower than an adjustment criterion; and an output unit configured to output parameter information indicating the adjustment-required parameter and effect information indicating an adjustment effect that is obtained when the adjustment-required parameter is adjusted. In this way, it is possible to educate a training assistant, who assists a trainee when the trainee performs rehabilitation by using a walking training apparatus, in order to enable the training assistant to appropriately assist the trainee.

The determination unit can determine, as the adjustment-required parameter, a parameter of which the frequency of adjustments is lower than a frequency with which a training assistant whose trainee shows a satisfactory degree of recovery make adjustments. In this way, it is possible to output, as the adjustment-required parameter, a parameter with which the degree of recovery of a trainee is improved, and thereby to improve the educational effect even further.

The determination unit can determine, as the adjustment-required parameter, a parameter of which the frequency of adjustments is low for a symptom of the trainee. In this way, it is possible to output, as the adjustment-required parameter, a parameter that is desired to be adjusted while taking the symptom of the trainee into consideration, and thereby to improve the educational effect even further.

The determination unit can determine importance of the adjustment-required parameter, and the output unit can output the parameter information and the effect information according to the importance of the adjustment-required parameter. In this way, it is possible to output the information while changing the outputting method or the like depending on whether or not the adjustment-required parameter is one that is important to improve the training result in the walking training apparatus, and thereby to improve the educational effect even further.

The determination unit can determine whether or not a parameter that is associated beforehand with a parameter adjusted by the walking training apparatus as a parameter that is recommended to be adjusted at the same time as the adjusted parameter is regarded as the adjustment-required parameter. In this way, it is possible to output, as the adjustment-required parameter, a parameter that is desired to be adjusted at the same time as the adjusted parameter, and thereby to improve the educational effect even further.

The walking training apparatus is configured so that a training mode indicating a training policy can be set, and the determination unit can make a determination based on an adjustment criterion that changes according to the training mode. In this way, it is possible to output, as the adjustment-required parameter, a parameter that is desired to be adjusted according to the training mode, and thereby to improve the educational effect even further.

The output unit can output the parameter information and the effect information to a display device for parameter adjustment incorporated in the walking training apparatus. In this way, it is possible to enable the training assistant to visually recognize the adjustment-required parameter and the effect information with ease, and thereby to improve the educational effect even further.

The output unit can output a video content including the parameter information and the effect information to the display device. In this way, it is possible to show the adjustment-required parameter and the effect information to the training assistant so that he/she can easily understand them, and thereby to improve the educational effect even further.

The processing system may be a server system accessible from a terminal apparatus that is used by the training assistant or provided in the hospital. In this way, the training assistant can check the adjustment-required parameter and the effect information at a timing the training assistant desires and hence the educational effect can be improved even further.

The server system can output a video content including the parameter information and the effect information to the terminal apparatus. In this way, it is possible to show the adjustment-required parameter and the effect information so that the training assistant can easily understand them at a timing the training assistant desires, and thereby to improve the educational effect even further.

The processing system may be an apparatus incorporated in the walking training apparatus. In this way, it is possible to educate, by using only the walking training apparatus, the training assistant so that he/she can appropriately assist the trainee.

A second exemplary aspect is a walking training system including: a processing system, the processing system being, among the processing systems according to the first aspect, the sever system; and a walking training apparatus connected to the processing system, in which the output unit outputs the parameter information and the effect information to the walking training apparatus side. In this way, it is possible to educate the training assistant by using a common server apparatus for a plurality of walking training apparatuses.

A third exemplary aspect is a processing method including: a determination step of determining an adjustment-required parameter, the adjustment-required parameter being, among parameters that can be adjusted in a walking training apparatus, a parameter of which a frequency of adjustments by a training assistant who assists a trainee performing walking training in the walking training apparatus or by an assistant in a hospital other than the training assistant is lower than an adjustment criterion; and an outputting step of outputting parameter information indicating the adjustment-required parameter and effect information indicating an adjustment effect that is obtained when the adjustment-required parameter is adjusted. In this way, it is possible to educate a training assistant, who assists a trainee when the trainee performs rehabilitation by using a walking training apparatus, in order to enable the training assistant to appropriately assist the trainee.

A fourth exemplary aspect is a program for causing a computer incorporated in or externally connected to a walking training apparatus to perform: a determination step of determining an adjustment-required parameter, the adjustment-required parameter being, among parameters that can be adjusted in a walking training apparatus, a parameter of which a frequency of adjustments by a training assistant who assists a trainee performing walking training in the walking training apparatus or by an assistant in a hospital other than the training assistant is lower than an adjustment criterion; and an outputting step of outputting parameter information indicating the adjustment-required parameter and effect information indicating an adjustment effect that is obtained when the adjustment-required parameter is adjusted. In this way, it is possible to educate a training assistant, who assists a trainee when the trainee performs rehabilitation by using a walking training apparatus, in order to enable the training assistant to appropriately assist the trainee.

According to the present disclosure, it is possible to provide a processing system capable of educating a training assistant, who assists a trainee when the trainee performs rehabilitation by using a walking training apparatus, in order to enable the training assistant to appropriately assist the trainee. Further, according to the present disclosure, it is possible to provide a walking training system including the above-described processing system, and provide a processing method and a program capable of providing such education.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 8 shows another example of an image shown to a training staff member in the process shown in FIG. 6.

DESCRIPTION OF EMBODIMENTS

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem.

First Embodiment

A first embodiment will be described hereinafter with reference to the drawings.
(System Configuration)

Figure 1:
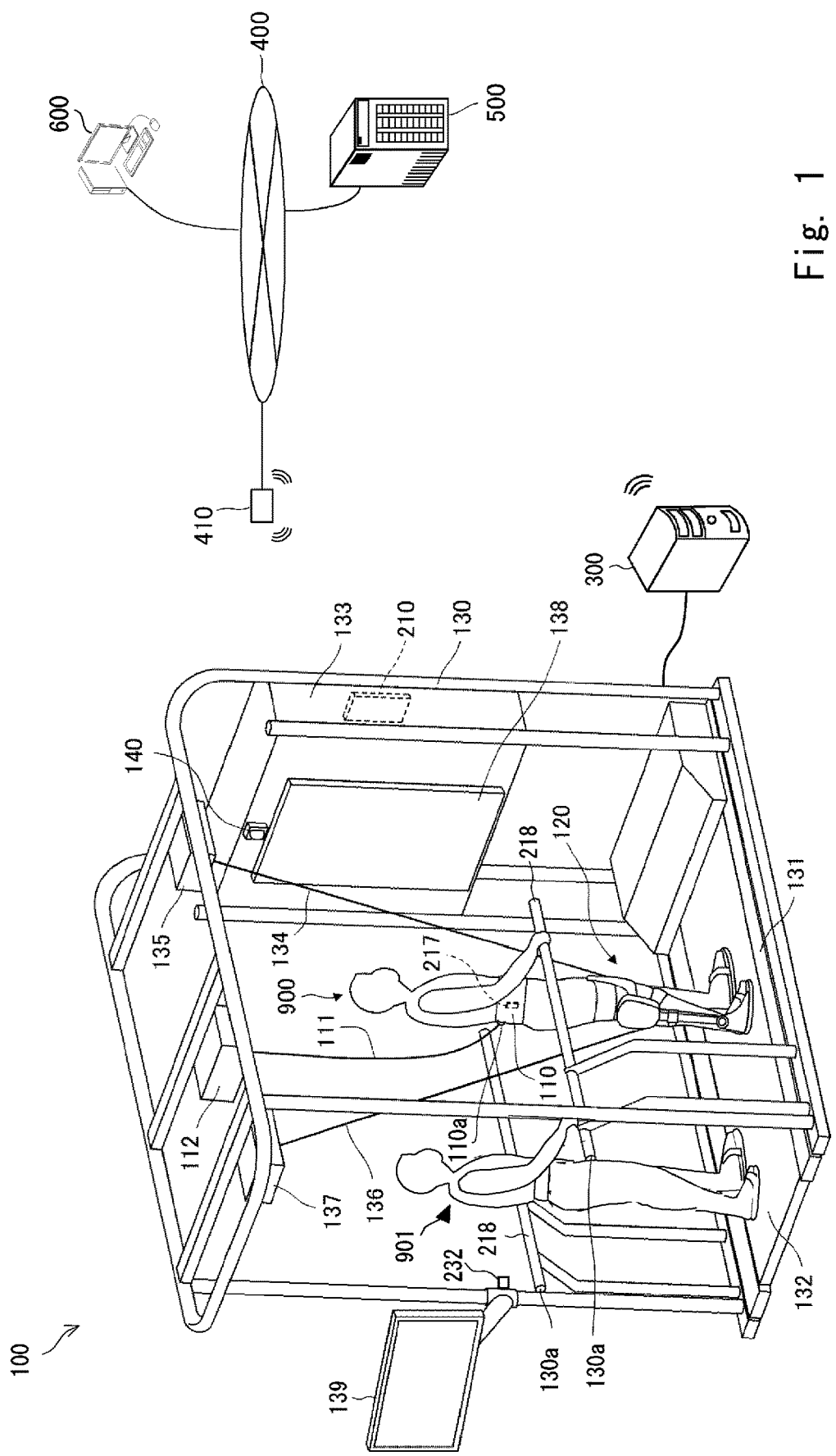
FIG. 1 is a general concept diagram showing an example of a configuration of a rehabilitation support system according to a first embodiment.

FIG. 1 is a general concept diagram showing an example of a configuration of a rehabilitation support system according to a first embodiment. The rehabilitation support system (the rehabilitation system) according to this embodiment may include, as main components, a walking training apparatus 100, an external communication apparatus 300, and a server (a server apparatus) 500.

The walking training apparatus 100 is a specific example of a rehabilitation support apparatus that supports rehabilitation performed by a trainee (a user) 900, and in particular a specific example of a waking training apparatus that supports walking training. The walking training apparatus 100 is an apparatus by which the trainee 900, who is, for example, a hemiplegic patient suffering from paralysis in one of his/her legs, does walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like. As shown as an example above, the training staff member 901 is a person(s).

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who does a walking training, gets on the belt 132 and tries walking in accordance with the movement of the belt 132. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height and width (i.e., distance therebetween). Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and/or moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The walking training apparatus 100 includes a fall-prevention harness apparatus as a safety apparatus, which includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on. Further, an emergency stop button 232 is provided near the management monitor 139. When the training staff member 901 pushes the emergency stop button 232, the walking training apparatus 100 immediately stops its operation.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

The overall control unit 210 generates rehabilitation data that may include setting parameters related to the training setting, various data related to the moving leg output from the walking assistance apparatus 120 as a result of training, and so on. The rehabilitation data may include, for example, data indicating the training staff member 901 or indicating his/her years of experience, level of proficiency, etc., data indicating the symptom, the walking ability, the degree of recovery, etc., of the trainee 900, various data output from sensors and the like provided outside the walking assistance apparatus 120. Note that details of the rehabilitation data will be described later.

The external communication apparatus 300 is a specific example of transmission means for transmitting the rehabilitation data to the outside. The external communication apparatus 300 may have a function of receiving and temporarily storing rehabilitation data output from the walking training apparatus 100 and a function of transmitting the stored rehabilitation data to the server 500.

The external communication apparatus 300 is connected to the control panel 133 of the walking training apparatus 100 through, for example, a USB (Universal Serial Bus) cable. Further, the external communication apparatus 300 is connected to a network 400 such as the Internet or an intranet through a wireless communication apparatus 410 by, for example, a wireless LAN (Local Area Network). Note that the walking training apparatus 100 may be equipped with a communication apparatus instead of using the external communication apparatus 300.

The server 500 is a specific example of an apparatus that implements some of the functions of a later-described processing apparatus (processing system) according to this embodiment. Further, the server 500 is a specific example of storage means for storing rehabilitation data, and is connected to the network 400 and has a function of accumulating rehabilitation data received from the external communication apparatus 300. The functions of the server 500 will be described later. Further, as shown in FIG. 1, the rehabilitation support system may include a terminal apparatus (an information processing apparatus) 600 such as a PC (Personal Computer) and a smartphone by which a user (e.g., a training staff member) peruses (or browses) rehabilitation data and the like accumulated in the server 500 through the network 400. The terminal apparatus 600 may be connected to the network 400 through a cable or wirelessly.

Figure 2:
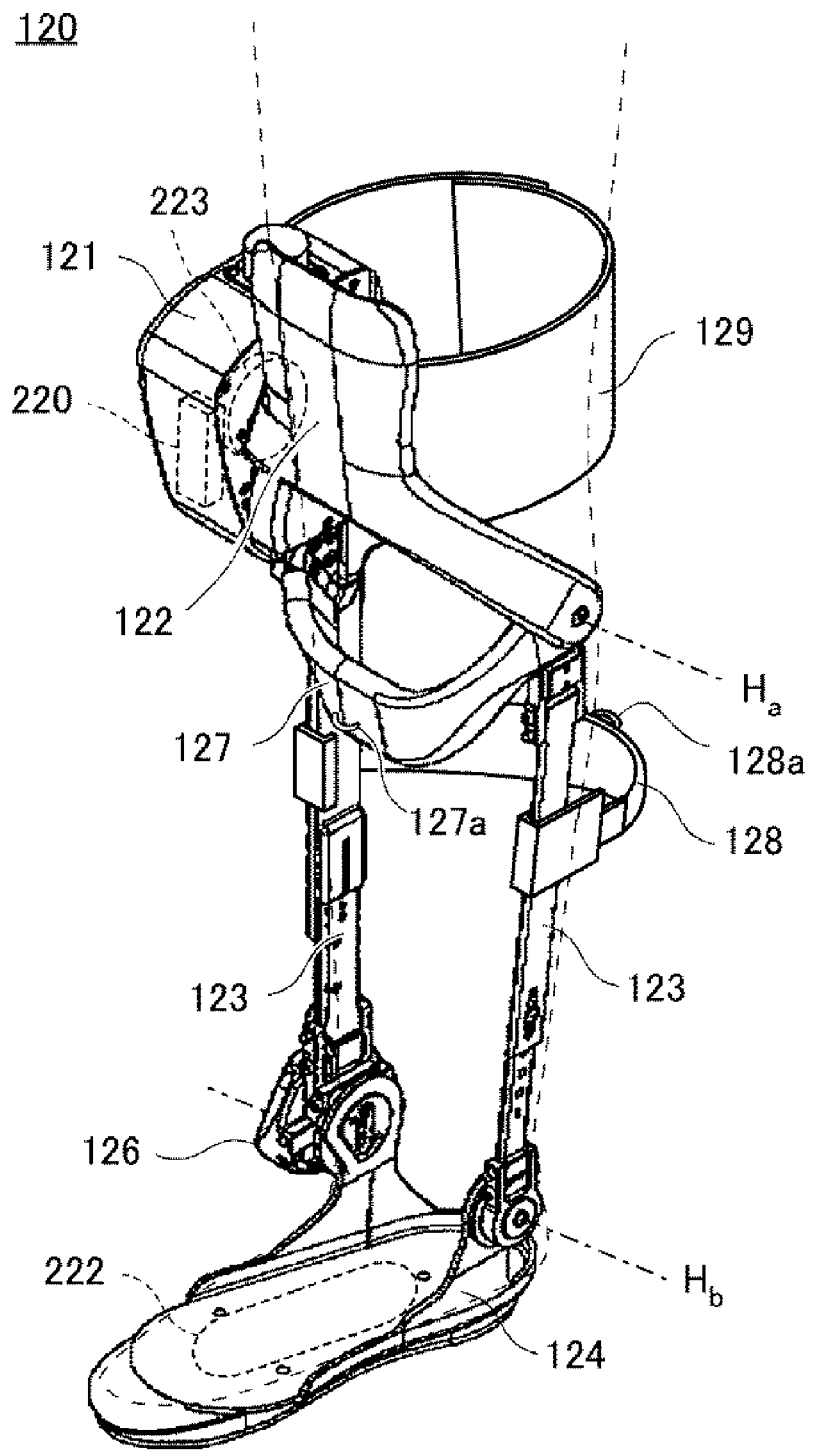
FIG. 2 is a schematic perspective view showing an example of a configuration of a walking assistance apparatus in the rehabilitation support system shown in FIG. 1.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the figure. The motor of the control unit 121 rotates according to an instruction from the assistance control unit 220, and by doing so, force the upper-leg frame 122 and the lower-leg frame 123 to open relative to each other around the hinge axis $H_a$ or force them to close relative to each other. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
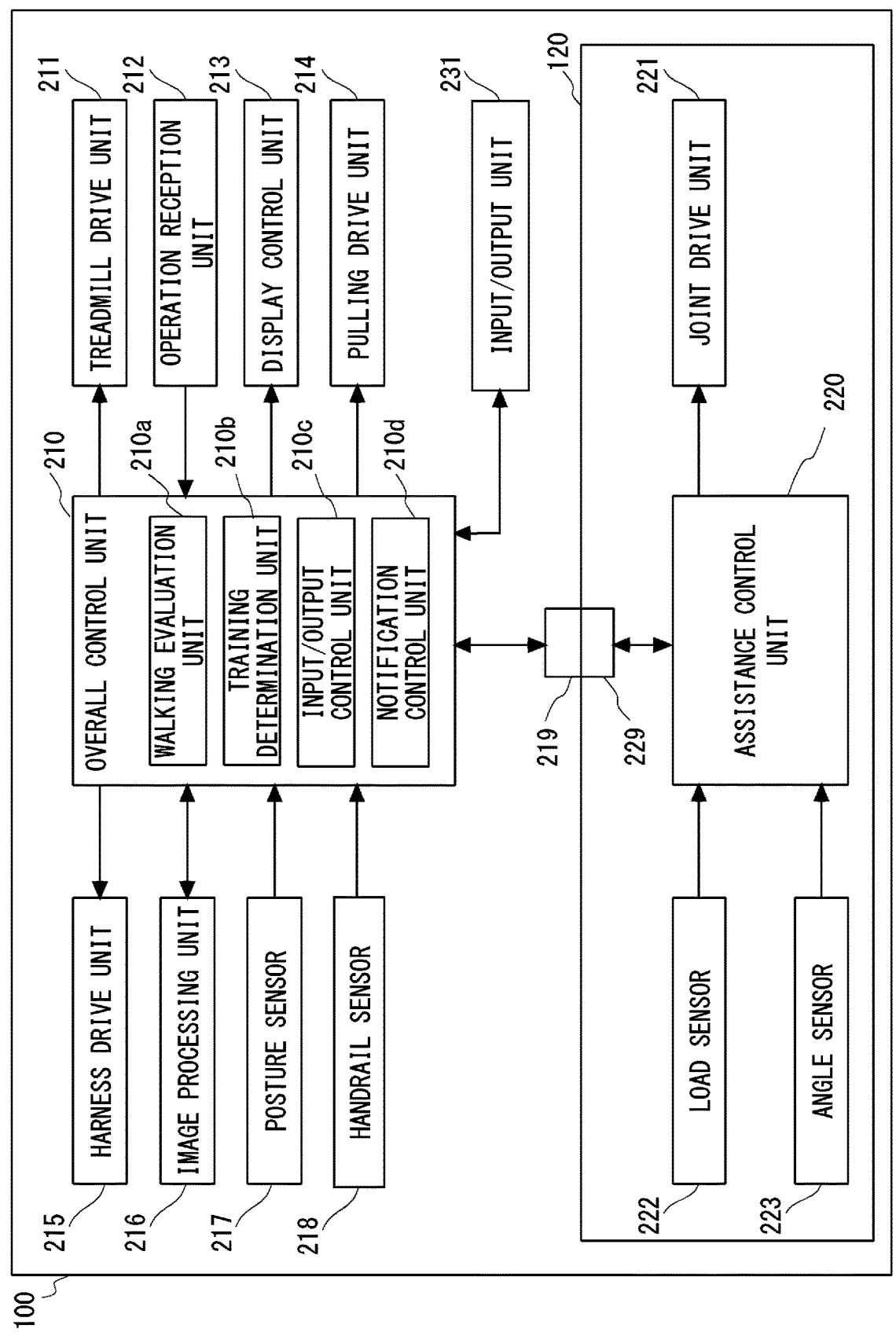
FIG. 3 is a block diagram showing an example of a system configuration of a walking training apparatus in the rehabilitation support system shown in FIG. 1.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input/output unit 231, and a walking assistance apparatus 120.

The overall control unit 210 is, for example, an MPU (Micro Processing Unit) and controls the overall operations of the apparatus by executing a control program loaded from a system memory. The overall control unit 210 may include a walking evaluation unit 210a, a training determination unit 210b, an input/output control unit 210c, and a notification control unit 210d, all of which will be described later.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The overall control unit 210 also serves as a function execution unit that performs various arithmetic operations and controls related to the overall control. The walking evaluation unit 210*a* evaluates whether the walking motion of the trainee 900 is abnormal or not by using data acquired from various sensors. The training determination unit 210*b* determines a training result of a series of walking trainings based on, for example, a cumulative number of the abnormal walking evaluated by the walking evaluation unit 210*a*. The overall control unit 210 can generate, as part of the rehabilitation data, a result of this determination or the cumulative number of the abnormal walking, based on which the determination result has been obtained.

Note that the determination method, including its criterion, is not limited to any particular methods. For example, the determination can be made by comparing an amount of movement of the paralyzed body part with a reverence value in each walking phase. Note that the walking phases are defined, for example, by classifying (i.e., dividing) one walking cycle of the diseased leg (or a normal leg) into a stance phase in a stance state, a transition phase from the stance phase to a swing phase in a swing state, the swing phase, a transition phase from the swing phase to the stance phase, etc. The walking phase can be classified (determined) based on, for example, the detection result of the load sensor 222 as described above. Note that although the walking cycle can be regarded as one cycle including a stance phase, a transitional phase, a swing phase, and another transitional phase as described above, any of these phases can be defined as the start phase. Alternatively, the walking cycle can be regarded as one cycle including, for example, a double-leg support state, a single-leg (diseased-leg) support state, a double-leg support state, and a single-leg (normal-leg) support state. Even in this case, any state may be defined as the start state.

Further, the walking cycle in which attention is paid to the right leg or the left leg (the normal leg or the diseased leg) can be further subdivided. For example, the stance phase can be divided into an initial ground contact and other four sub-phases, and the swing phase can be divided into three sub-phases. The initial ground contact means a moment when the observed foot touches the floor, and the four sub-phases of the stance phase means a load response phase, a mid-stance phase, a terminal stance phase, and a pre-swing phase. The load response phase is a period from the initial ground contact to when the opposite foot comes off the floor (opposite-foot-off). The mid-stance is a period from the opposite-foot-off to when the heel of the observed foot comes off the floor (heel-off). The terminal stance phase is a period from the heel-off to an initial ground contact on the opposite side. The pre-swing phase is a period from the initial ground contact on the opposite side to when the observed foot comes off the floor (foot-off). The three sub-phases of the swing phase mean an initial swing phase, a mid-swing phase, and a terminal swing phase. The initial swing phase is a period from the end of the pre-swing phase (the aforementioned foot-off) to when both feet cross each other (foot crossing). The mid-swing phase is a period from the foot crossing to when the tibia becomes vertical (vertical tibia). The terminal swing phase is a period from the vertical tibia to the next initial ground contact.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program according to an instruction from the overall control unit 210. Further, the assistance control unit 220 notifies the overall control unit 210 of the state of the walking assistance apparatus 120 through the communication connection IFs 229 and 219. Further, the assistance control unit 220 performs control of walking assistance apparatus 120, such as the start/stop thereof, in response to a command from the overall control unit 210.

The joint drive unit 221 includes a motor of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The load sensor 222 detects the magnitude and the distribution of the vertical load (e.g., the vertical pressure) applied to the sole of the trainee 900 and transmits a detection signal to the assistance control unit 220 as described above. The assistance control unit 220 receives and analyzes the detection signal, and thereby determines the swing/stance state and estimates the switching therebetween.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

The input/output unit 231 includes, for example, a USB (Universal Serial Bus) interface and is a communication interface for connecting to an external apparatus (an external communication apparatus 300 or other external apparatus). The input/output control unit 210*c* of the overall control unit 210 communicates with the external apparatus through the input/output unit 231, rewrites the above-described control program stored in the overall control unit 210 and the control program stored in the assistance control unit 220, receives commands, outputs generated rehabilitation data, and so on. The walking training apparatus 100 communicates with the server 500 through the input/output unit 231 and the external communication apparatus 300 under the control of the input/output controller 210*c*. For example, the input/output control unit 210*c* can control the transmission of rehabilitation data to the server 500 and the reception of a command from the server 500 through the input/output unit 231 and the external communication apparatus 300.

When it is necessary to provide a notification to the training staff member 901, the notification control unit 210*d* provides the notification from the management monitor 139 or a separately-provided speaker(s) by controlling the display control unit 213 or a separately-provided sound control unit or the like. The aforementioned situation where it is necessary to provide a notification to the training staff member 901 may include a situation where a command for providing a notification is received from the server 500. Details of the notification will be described later.

Figure 4:
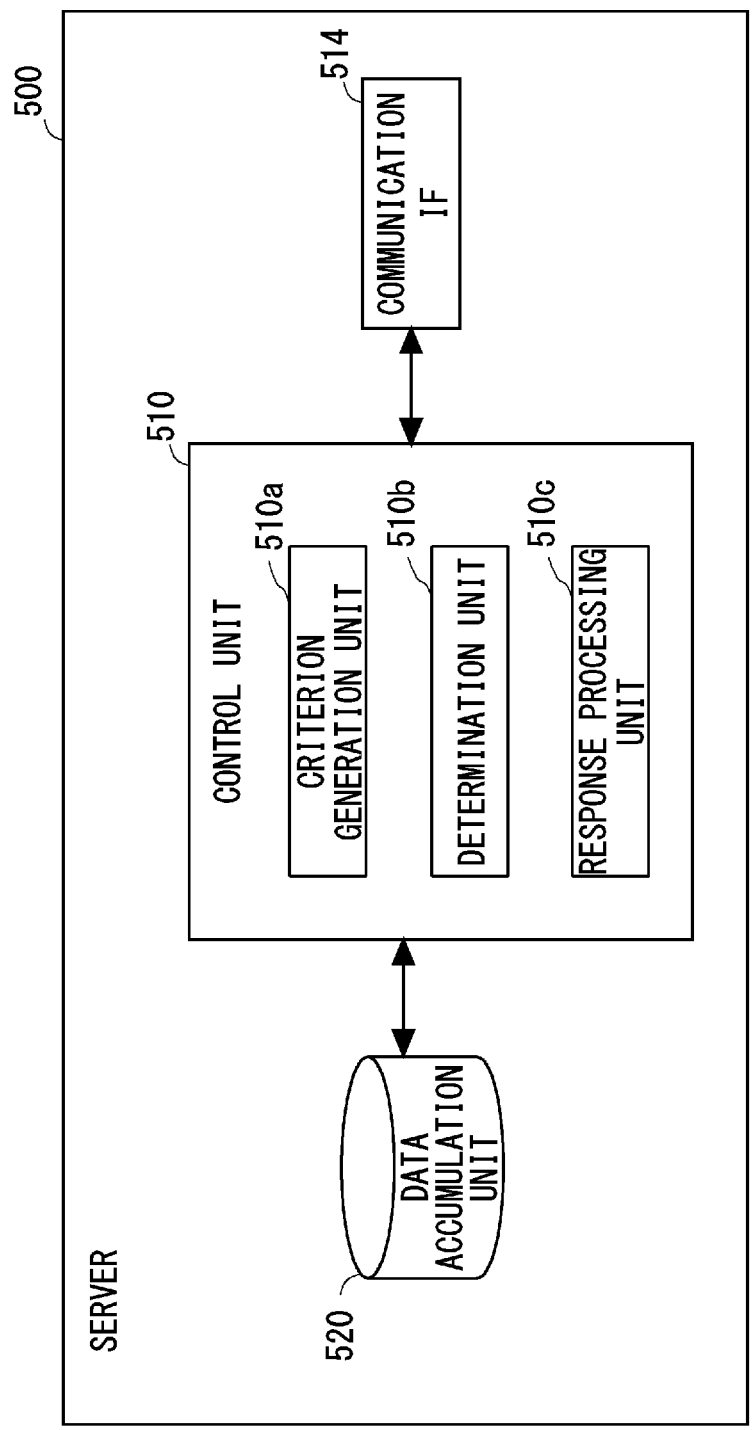
FIG. 4 is a block diagram showing an example of a configuration of a server in the rehabilitation support system shown in FIG. 1.

Next, details of the server 500, which is an example of the processing apparatus according to this embodiment, will be described with reference to FIG. 4 as well. FIG. 4 is a block diagram showing an example of a configuration of the server 500. Note that the processing apparatus according to this embodiment and those according to second and third embodiments described later may be formed as a processing system by using a plurality of apparatuses (a plurality of apparatuses over which functions are distributed).

As shown in FIG. 4, the server 500 can include a control unit 510, a communication IF 514, and a data accumulation unit 520. The control unit 510 is, for example, an MPU and controls the server 500 by executing a control program loaded from a system memory. The control unit 510 may include a criterion generation unit 510a, a determination unit 510b, and a response processing unit 510c, all of which will be described later. Further, in this case, the above-described control program includes a program(s) for implementing the functions of the control unit 510, including the functions of these units 510a to 510c.

The communication IF 514 includes, for example, a wired LAN interface and is a communication interface for connecting to the network 400. As described above, the walking training apparatus 100 transmits various rehabilitation data to the server 500 through the external communication apparatus 300. The server 500 may be configured so as to receive rehabilitation data from a plurality of walking training apparatuses 100. In this way, the server 500 can collect a number of rehabilitation data. For example, the control unit 510 can receive rehabilitation data from the walking training apparatus 100 through the communication IF 514. Further, the control unit 510 can transmit a command to the walking training apparatus 100.

The data accumulation unit 520 includes a storage device such as an HDD (Hard Disk Drive) or an SSD (Solid State Drive) and stores rehabilitation data therein. The control unit 510 writes the rehabilitation data received from the external communication apparatus 300 into the data accumulation unit 520 through the communication IF 514.

The processing apparatus according to this embodiment includes a determination unit and an output unit. Further, the server 500 may be configured so that the determination unit 510b and the response processing unit 510c serve as the determination unit and the output unit, respectively. The criterion generation unit 510a in the server 500 generates a criterion (an adjustment criterion described later) used in a determination process performed by the determination unit 510b based on the rehabilitation data. An example of the criterion generation process will be described later together with the rehabilitation data.

The response processing unit 510c receives rehabilitation data including at least parameters (setting parameters) that can be adjusted in the walking training apparatus 100 from the walking training apparatus 100 through the communication IF 514. The determination unit 510b inputs this rehabilitation data and determines an adjustment-required parameter(s) from among the setting parameters that are included in this rehabilitation data and can be adjusted in the walking training apparatus 100. That is, the determination unit 510b determines, for each of the input setting parameters, whether or not the setting parameter is a parameter that needs to be adjusted.

The adjustment-required parameter may be a parameter of which the frequency of adjustments by the training staff member 901 who assists the trainee 900 performing walking training in the walking training apparatus 100 is lower than the adjustment criterion. An example in which the adjustment-required parameter is such a parameter will be described hereinafter. However, the adjustment-required parameter may be a parameter of which the frequency of adjustments by a staff member other than the training staff member in the hospital is lower than the adjustment criterion. Note that the staff member other than the training staff member means a staff member other than the training staff member who actually assists the training. Examples of the staff member other than the training staff member include a staff member who sets standard parameter values determined by a doctor of the hospital.

When the determination unit 510b determines that there is an adjustment-required parameter(s), the response processing unit 510c reads effect information that is stored in the data accumulation unit 520 in advance and indicates an adjustment effect that is obtained when that adjustment-required parameter is adjusted. Then, the response processing unit 510c outputs (returns) the effect information together with the parameter information indicating the adjustment-required parameter to the walking training apparatus 100 side through the communication IF 514. When there are a plurality of adjustment-required parameters, the response processing unit 510c returns parameter information and effect information for each of the adjustment-required parameters. The reply can be carried out by using a command for conveying the information or a command for instructing to output (e.g., display) the information.

Upon receiving the command including the information from the server 500, the walking training apparatus 100 outputs the information so that the training staff member 901 can recognize the information. For this outputting process, the walking training apparatus 100 may include, as a main component, a display unit (or an audio output unit) exemplified by the notification control unit 210d, the display control unit 213, and the management monitor 139 (or, an audio control unit and a speaker(s)). Examples of the outputting process include a process for displaying the parameter information and the effect information on the management monitor 139 and a process for outputting a voice of a sound representing the information from a speaker(s) (not shown). Note that what kind of outputting process should be performed may be determined beforehand according to the above-described command. The display (i.e., displayed images) may be controlled by the display control unit 213 and the voice output (or the sound output) may be controlled by an audio control unit (not shown).

The management monitor 139 is an example of a display device for parameter adjustment incorporated in the walking training device 100. By the visual outputting process, it is possible to enable the training staff member 901 to visually recognize the adjustment-required parameter and the effect information with ease, and thereby to improve the educational effect even further. Further, the aforementioned speaker(s) may be, for example, a wireless earphone(s) (e.g., a bone-conduction-type earphone(s)) attached to an ear(s) or the like of the training staff member 901 in order to prevent the trainee 900 from hearing the sound or the voice.

Further, the information to be displayed on the aforementioned display device may be a video content including the parameter information and the effect information. Similarly to the effect information described above, such video contents may be created in advance and stored in the data accumulation unit 520 in advance. In this way, it is possible to show the adjustment-required parameter and the effect information to the training staff member 901 so that he/she can easily understand them, and thereby to improve the educational effect even further. Needless to say, the video content may include a voice of a sound that can be output from the audio output unit.

Further, the video content may be a video image that is obtained by selecting a characteristic part(s) of an actual video image of the trainee 900 (e.g., a part(s) where a certain symptom occurred), or may include such a video image. In particular, by having the training staff member 901 check such a video content possibly with the trainee 900 during a break or immediately after the training, it becomes possible to adjust a setting parameter(s) to a more desirable value(s) in the next practice or in the next training.

As shown in the above example, the above-described output unit included in the processing apparatus according to this embodiment outputs the parameter information indicating an adjustment-required parameter determined by the determination unit 510b and the effect information indicating an adjustment effect that is obtained when the adjustment-required parameter is adjusted. As described above, the processing apparatus according to this embodiment may be the server 500. The processing apparatus according to this embodiment can also be referred to as an output apparatus because it outputs the above-described information. According to this embodiment, by the above-described configuration, it is possible to educate the training staff member 901, who assists a trainee 900 when the trainee 900 performs rehabilitation by using the walking training apparatus 100, in order to enable the training staff member 901 to appropriately assist the trainee 900.

(Rehabilitation Data)

Prior to describing specific examples of the criterion generation unit 510a, the determination unit 510b, and the response processing unit 510c, rehabilitation data that the server 500 can collect for the criterion generation process, the determination process, or the like is described hereinafter. The rehabilitation data that the server 500 can collect mainly includes (1) setting parameters of the walking training apparatus 100, (2) detection data detected by sensors and the like provided in the walking training apparatus 100, (3) data related to the trainee 900, and (4) data related to the training staff member 901. The rehabilitation data of the above-described items (1) to (4) may be collected in association with their acquisition date. Further, the detection data or the setting parameter may be collected as time-series log data, or may be, for example, feature values extracted from data acquired at certain time intervals.

The rehabilitation data is mainly data that is obtained by an input operation, an automatic input, a measurement by a sensor, or the like in the walking training apparatus 100. Further, the rehabilitation data may also include recorded image data recorded by the camera 140. Note that the rehabilitation data may be data acquired on each day of rehabilitation. In this case, the rehabilitation data can be referred to as daily report data. In the following description, it is assumed that the server 500 collects rehabilitation data generated by the walking training apparatus 100. However, it is also possible to configure the server 500 so as to acquire a part of rehabilitation data from an apparatus other than the walking training apparatus 100 such as another server. Here, the part of the rehabilitation data may be, for example, a detail of data of the above-described item (3) such as a symptom of the trainee 900, or a detail of data of the above-described item (4) such as years of experience of a PT (Physical Therapist). The former can be stored in other servers as medical record information of the trainee 900 and the latter can be stored in other servers as a personal history of a PT.

In the stage in which the criterion generation process is performed (i.e., in the criterion generation stage), the server 500 may receive rehabilitation data from the walking training apparatus 100 when new rehabilitation data is generated or at regular intervals such as on every day or in every week. The type of rehabilitation data to be used (the content included in the rehabilitation data) in the criterion generation process stage may be changed from that in the operation stage including the determination process and the outputting process. For example, in the operation stage, the server 500 may receive rehabilitation data including the setting parameter of the above-described item (1) from the walking training apparatus 100 at the start of training (or at the time when the trainee becomes ready to start the training), and may receive data of the above-described item (1) that is changed during the training. Further, the transmission and the reception of rehabilitation data may be initiated by either the walking training apparatus 100 or the server 500.

The above-described item (1) is described.

The data of the above-described item (1) can be defined as training data of the trainee 900 that is acquired during rehabilitation in the walking training apparatus 100 together with the detection data of the above-described item (2).

The setting parameter of the walking training apparatus 100 is, for example, data that is input by an operator or automatically set in order to define the actions performed by the walking training apparatus 100. Note that as described above, it is assumed that the operator is typically the training staff member 901 who actually attends the training of the trainee 900. Therefore, the following description is given on the assumption that the operator is the training staff member 901. Further, the training staff member 901 is often a PT (Physical Therapist). Therefore, the training staff member 901 may also be referred to simply as the "PT" in the following description.

In the walking training apparatus 100, the level of difficulty of walking training can be adjusted by the setting parameters. Note that the setting parameters may include a parameter indicating the level of difficulty, and in this case, some or all of the other setting parameters may be changed according to the change in the level of difficulty. The training staff member 901 increases the level of difficulty of the walking training as the trainee 900 recovers. That is, the training staff member 901 reduces the assistance provided by the walking training apparatus 100 as the walking ability of the trainee 900 improves. Further, the training staff member 901 increases the assistance when an abnormality is found during the walking training. As the training staff member 901 appropriately adjusts the setting parameters, the trainee 900 can perform appropriate walking training and hence perform the rehabilitation more efficiently.

Specific examples of the setting parameters are shown hereinafter.

Examples of the setting parameters include a partial weight-supported amount [%], vertical positions of the handrails 130a [cm], left/right positions of the handrails 130a [cm], presence/absence of a hip joint, ankle joint plantar flexion limitation [deg], and ankle joint dorsiflexion limitation [deg]. Further, the examples of the setting parameters also include a treadmill speed [km/h], swinging assistance [level], and a swinging forward/backward ratio [forward/backward]. Further, the examples of the setting parameters also include knee extension assistance [level], a knee flexing angle [deg], a knee flexing/extending time

[sec], a wedge thickness (or a shoe lift) [mm], a weight-off threshold [%], and a load threshold [%]. Further, the examples of the setting parameters also include an inclination of the belt of the treadmill [deg], assistance for a motion of a joint by the walking assistance apparatus [level], a frequency with which assistance for a motion of a joint or swinging assistance by the walking assistance apparatus is provided, a condition for determining abnormal or normal walking (e.g., a determination threshold), a condition for determining that the trainee will fall down or is likely to fall down (e.g., a determination threshold), and a condition for an occurrence of abnormal or normal walking in the case where a notification is provided in association with the abnormal or normal walking (a frequency of occurrences, an occurrence threshold, etc.). Note that the notification may be any of a sound, a vibration, a display, or the like, and may include some or all of them. Note that any type of unit may be used as the unit of data included in rehabilitation data, including the above-shown setting parameters.

The partial weight-supported amount is a ratio at which the weight of the trainee 900 is supported by making the harness pulling unit 112 pull the harness wire 111. The training staff member 901 sets the partial weight-supported amount to a lower value as the desired level of difficulty of the walking training increases. The vertical positions and the left/right positions of the handrails 130a are amounts of adjustments of the handrails 130a from reference positions. The presence/absence of a hip joint is whether or not the hip joint is attached. The ankle joint plantar flexion limitation and the ankle joint dorsiflexion limitation define an angular range in which the lower-leg frame 123 and the sole frame 124 can rotate around the hinge axis $H_b$. The ankle joint plantar flexion limitation corresponds to an upper-limit angle on the front side and the ankle joint dorsiflexion limitation corresponds to a maximum angle on the rear side. That is, the ankle joint plantar flexion limitation and the ankle joint dorsiflexion limitation are limit values of angles at which the ankle joint is bent in a direction in which the toe is lowered and a direction in which the toe is raised, respectively. The training staff member 901 sets the values of the ankle joint plantar flexion limitation and the ankle joint dorsiflexion limitation so that the angular range increases as the desired level of difficulty of the walking training increases.

The treadmill speed is a walking speed on the treadmill 131. The training staff member 901 sets the treadmill speed to a higher value as the desired level of difficulty of the walking training increases. The swinging assistance is a level corresponding to the pulling force applied by the front wire 134 when the leg is swung. Further, the maximum pulling force is increased as this level is raised. The training staff member 901 sets the swinging assistance to a lower level as the desired level of difficulty of the walking training increases. The swinging forward/backward ratio is a ratio between the pulling force by the front wire 134 and the pulling force by the rear wire 136 when the leg is swung.

The knee extending assistance is a level corresponding to the driving torque of the joint drive unit 221 that is applied to prevent the knee from buckling during the stance state. Further, the driving torque is increased as this level is raised. The training staff member 901 sets the knee extending assistance at a lower level as the desired level of difficulty of the walking training increases. The knee flexing angle is an angle at which knee extending assistance is provided. The knee flexing/extending time is a period during which the knee extending assistance is provided. Further, when this value is large, the knee is assisted so that it is slowly flexed and extended, whereas when this value is small, the knee is assisted so that it is quickly flexed and extended.

The wedge thickness is a height of a member such as a cushion provided in the sole of the shoe of the leg of the trainee 900 opposite to the paralyzed leg thereof (i.e., the leg on the side on which the walking assistance apparatus 120 is not attached). The weight-off threshold is one of the thresholds for the load (i.e., the pressure) applied to the sole. When the load becomes smaller than this threshold, the swinging assistance is cancelled (i.e., ceased). The load threshold is one of the thresholds for the load applied to the sole. When the load exceeds this threshold, the swinging assist is provided (i.e., started). As described above, the walking assistance apparatus 120 may be configured so that the flexing/extending motion of the knee can be adjusted by four setting parameters, i.e., the knee flexing angle, the knee flexing/extending time, the weight-off threshold, and the load threshold.

Further, the walking training apparatus 100 may also be configured so that setting values of various parameters such as a load and an angle, a target value, a target achievement rate, a target achievement timing, etc. are fed back to the trainee and/or training staff member by a sound output from a speaker(s) (not shown). The above-described setting parameters may include parameters for other settings such as presence/absence of a feedback sound and its volume.

In addition, the above-described setting parameters may not be setting parameters directly related to the level of difficulty of the training. For example, the above-described setting parameters may be setting values for images, music, a type of game, a level of difficulty of game, etc. that are provided through the training monitor 138 or a speaker(s) (not shown) in order to motivate the trainee 900.

Note that the above-described setting parameters are merely examples and other setting parameters may be used. Further, some of the above-described setting parameters may not be used. Further, although the above-described setting parameters include many parameters for adjusting the level of difficulty of the training as described above, they may also include parameters unrelated to the level of difficulty. For example, the walking training apparatus 100 may be configured so as to display an alert icon image that is to be displayed on the training monitor 138. Further, examples of the setting parameters unrelated to the level of difficulty include parameters for increasing the degree of concentration of the trainee 900 on the training, such as the size and the displaying interval of the above-described alert icon image. Further, time information such as date and time at which the setting operation is performed or timing information other than the time (e.g., information indicating a distinction between the stance phase, the swing phase, etc. in one walking cycle) can be added to the above-described setting parameters.

The above-described item (2) is described.

The detection data of the above-described item (2) can be defined as training data of the trainee 900 that is acquired during the rehabilitation in the walking training apparatus 100 together with the data of the above-described item (1).

A typical example of the detection data is sensor data. The sensor data is sensor values detected by various sensors of the walking training apparatus 100. For example, the sensor data includes an inclination angle of the trunk detected by the posture sensor 217, a load and an inclination angle detected by the handrail sensor 218, an angle detected by the angle sensor 223, etc. The sensors that output the sensor data are an acceleration sensor, an angular-velocity sensor, a position sensor, an optical sensor, a torque sensor, a weight sensor, etc. Further, encoders provided in motors of the winding mechanisms or the like of the front wire 134, the rear wire 136, and the harness wire 111 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 900 by performing image processing based on an image taken by shooting at least an area including the eyes of the trainee 900, or obtained by determining the orientation (upward/downward etc.) of the face of the trainee 900 based on an image taken by shooting at least the face. Such data may also be included in the aforementioned detection data. Further, the detection data may be audio data (voice data) acquired by a voice acquisition unit, such as a microphone, that acquires a voice of the trainee 900 or the training staff member 901, text data obtained by performing a voice analysis on the voice data, or data obtained by analyzing the text data. The voice of the training staff member 901 may include an encouraging talk to the trainee 900 about, for example, how to correct his/her walking. Further, the sensor data may be data obtained by detecting brain waves of the trainee 900 by using an electroencephalograph, or may be data obtained by detecting brain waves of the training staff member 901 by using an electroencephalograph.

Further, the line-of-sight detection sensor, a shooting unit that takes the above-described image, a microphone, and the like can be disposed in the walking training apparatus 100 itself. Alternatively, they can also be disposed in, for example, an eyeglass-type wearable terminal that is worn by the trainee 900. This terminal may include a wireless communication unit that wirelessly transmits and receives data by a wireless communication technique such as Bluetooth (Registered Trademark). Further, the walking training apparatus 100 may also include a wireless communication unit. In this way, the walking training apparatus 100 can acquire data acquired by the wearable terminal through wireless communication. Although the electroencephalograph is limited to those having high detection accuracy, it may be disposed in the walking training apparatus 100 itself and configured so that the electroencephalogram of the trainee 900 and that of the training staff member 901 can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as a sensor, is not limited to those described above with reference to FIGS. 1 to 3 or those exemplified by the eyeglass-type wearable terminal. For example, the trainee 900 may wear clothes equipped with a wearable biosensor and/or a wearable touch sensor. Here, the clothes are not limited to those worn on the upper body. That is, they may be those worn on the lower body, a top-and-bottom set, or those attached to a part of the harness 110 or the like. Further, a wireless communication unit like the one described above is provided in each of the clothes and the walking training apparatus 100. In this way, the walking training apparatus 100 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 900, who is the wearer, made from the outside. That is, the wearable touch sensor can acquire data indicating information about a position where the training staff member 901 touched the trainee 900.

Further, the detection data is not limited to the values indicated by the detection signals detected by various sensors and the like. That is, they may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame 122 and the lower-leg frame 123 detected by the angle sensor 223. Further, the sensor data of the angle sensor may include an angular velocity that is obtained by differentiate the angle. The sensor data of the acceleration sensor may be a velocity that is obtained by integrating the acceleration or a position that is obtained by integrating the acceleration twice.

For example, the detection data may include the below-described average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill 131 or a value calculated from the drive signal in the treadmill drive unit 211. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff member 901 has assisted the trainee 900 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times].

Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill 131 that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the above-described detection data may not be used. That is, when the detection data is used as rehabilitation data, the server 500 needs to collect at least one detection data.

The above-described item (3) is described.

The data related to the trainee 900 (hereinafter referred to as trainee data) indicates, for example, a property of the trainee 900. Examples of the trainee data include an age, a gender, a physique (a height, a weight, etc.) of the trainee 900, information about a symptom, a Br. Stage, an SIAS, an initial walking FIM, and a latest walking FIM. Further, the trainee data may also include a name or an ID of the trainee 900. Further, the trainee data may also include preference information indicating a preference of the trainee 900 and personality information indicating his/her personality. Further, the trainee data may include, as the FIM, an exercise item other than those related to the walking ability, and may include a recognition item. That is, the trainee data may include various data indicating physical abilities of the trainee 900. Note that part or all of the trainee data may be referred to as body information, basic information, or trainee feature information.

Note that the symptom information may include information indicating an initial symptom, a time when the symptom appears, and a current symptom. Further, it can be considered that the trainee 900 needs to perform rehabilitation mainly because of at least one of the symptoms described above. However, symptoms that are unlikely to be directly related to the rehabilitation may also be included in the symptom information. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/ subarachnoid hemorrhage), etc.

The Br. Stage means a Brunnstrom Recovery Stage in which a recovery process of a hemiplegia is divided into six stages based on the observation. The trainee data may include, of the Br. Stage, lower-limb items that are main items related to the walking training apparatus 100. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

For example, a walking FIM is a general index indicating the degree of recovery. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 900 gradually increases. Note that the walking distance in the evaluation of the walking FIM is not limited to 50 m. For example, the walking distance may be 15 m.

As can be understood from the above description, the latest walking FIM used by the walking training apparatus 100 is used as not only an index indicating the physical ability of the trainee 900 but also an index indicating the degree of recovery of the trainee 900 from the start of the rehabilitation. The walking FIM is used as an index indicating the moving ability of the trainee 900 when no actuator is used, i.e., an index indicating his/her walking ability. In other words, the walking FIM is an important index in order to recognize the progress of the rehabilitation of the trainee 900. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee 900 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

As described above, the trainee data in the above-described item (3) may include index data about rehabilitation performed by the trainee 900 by using the walking training apparatus 100, including at least one of the symptom, the physical ability, and the degree of recovery of the trainee 900. Note that in general, data that can be included in both concepts of the physical ability and the degree of recovery, such as the latest walking FIM, may be included in one of them. However, such data can also be included in both of them. Note that the same applies to all the items of the rehabilitation data. Further, data of a given item can be handled as data of one or a plurality of the above-described items (1) to (4). Further, time information such as the date and time at which the walking FIM is acquired, e.g., the measurement date of the walking FIM may be added in the above-described trainee data.

The above-described item (4) is described.

The data about the training staff member 901 (hereinafter referred to as staff data) indicates, for example, a property of the training staff member 901. The staff data includes a name or an ID, an age, a gender, a physique (a height, a weight, etc.) of the training staff member 901, a name of a hospital to which the training staff member 901 belongs, and his/her years of experience as a PT or a doctor. The staff data may include, as data related to the assistance, a value that numerically represents the timing at which the trainee 900 is assisted.

Further, in the case where a plurality of training staff members simultaneously assist the rehabilitation, the rehabilitation data may include data of the plurality of staff members. Further, each staff data may include information indicating whether the staff member is the main training staff member or an assistance training staff member. In addition to or instead of such information, each staff data may include information indicating whether the staff member is a training staff member who performs a setting operation and/or image checking in the management monitor 139, or whether or not the staff member is a training staff member who just physically supports the trainee 900 by hand.

Further, the walking training apparatus 100 may be configured so that a user (e.g., a training staff member) can enter a rehabilitation plan for the trainee 900. Further, the data of the rehabilitation plan entered as described above may also be included as staff data related to the training staff member 901 who has entered the data or as rehabilitation data belonging to other categories. Further, the walking training apparatus 100 may be configured so that, to make it possible to cope with the change of the training staff member 901, a user can enter remarks and/or messages for assisting the training of the trainee 900 in the future. Further, the data entered as described above may also be included as staff data related to the training staff member 901 who has entered the data or as rehabilitation data belonging to other categories.

The reason for including these data in the rehabilitation data is that there are possible situations where a training staff member has been able to successfully carry out the training of the trainee 900 because of the presence of remarks and/or messages given by other skilled training staff members. Further, time information such as the date and time at which the rehabilitation plan is entered, e.g., the input date and time of the rehabilitation plan may be added in the above-described staff data.

(Criterion Generation Stage)

Figure 5:
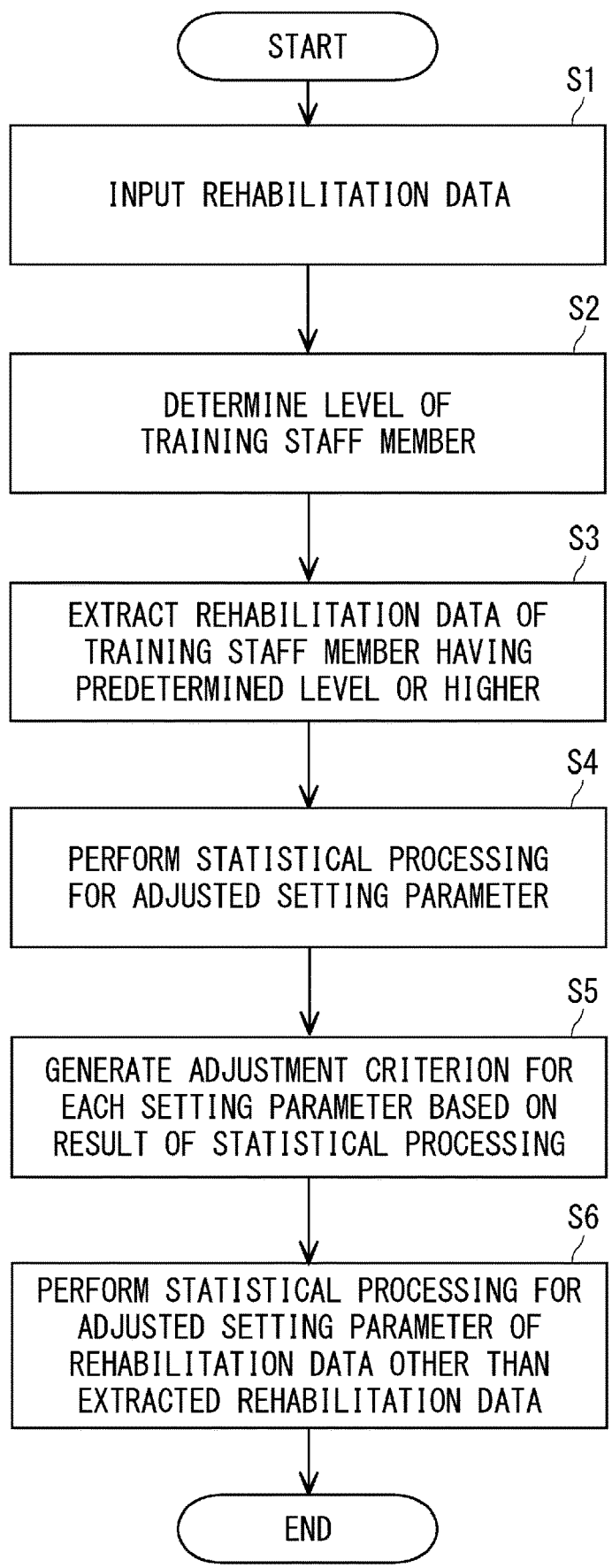
FIG. 5 is a flowchart for explaining an example of a criterion generation process performed in the rehabilitation support system shown in FIG. 1.

Next, details of the criterion generation process performed in the criterion generation unit 510a of the server 500 will be described with reference to FIG. 5. FIG. 5 is a flowchart for explaining an example of the criterion generation process performed in the server 500.

The server 500 collects rehabilitation data from a plurality of walking training apparatuses 100. Needless to say, these rehabilitation data are collected for training performed by a plurality of trainees 900. Then, the server 500 accumulates the collected rehabilitation data in the data accumulation unit 520. The criterion generation unit 510a generates data that is used as an adjustment criterion from part or all of the information included in the above-described rehabilitation data. The generation of the adjustment criterion will be described hereinafter in a concrete manner.

Firstly, a plurality of sets of data are prepared in the data accumulation unit 520 of the server 500. To that end, for example, the control unit 510 accumulates rehabilitation data collected in a predetermined period as one set of data in the data accumulation unit 520. For example, rehabilitation data collected in one walking training session or one practice of walking training may be prepared as one set of data. The rehabilitation data is data about rehabilitation that is performed by the trainee 900 by using the walking training apparatus 100 while being assisted as required by the training staff member 901. Note that in the following description, one set of data is also referred to simply as a data set.

Note that one walking training session is a series of trainings performed by one trainee 900. Further, after one walking training session is completed by the trainee 900, the next trainee 900 performs training in the same walking training apparatus 100. One walking training session usually takes about 20 to 60 minutes. One practice of walking training is one unit during which the trainee 900 continuously walks, included in one walking training session. One walking training session includes a plurality of walking training practices. For example, one practice takes about five minutes. Specifically, in one walking training session, the trainee 900 takes a five-minute break after every time he/she performs walking training for five minutes. That is, a walking training practice and a break are alternately repeated in one walking training session. The five-minute interval between breaks is the time for one practice. Needless to say, neither of the time for one training session and the time for one practice is limited to any particular time period. That is, they may be set as appropriate for each trainee 900.

Further, rehabilitation data collected in a period shorter than the period of one practice may be prepared as one data set, or rehabilitation data collected in a period longer than the period of one practice may be prepared as one data set. Needless to say, when attention is paid to only one of the collected data sets, there is a possibility that at least one of a setting parameter, staff data, and index data, which are required in the later-described step S2, is not included in the input rehabilitation data. In such a case, for example, it is possible to prepare a data set by using a value(s) in the immediately preceding data set. Further, data that is obtained before the training staff member 901 changes the setting parameter or gives an encouraging talk or before the index data is changed may be prepared as one data set.

Further, as described above, the data set is not limited to raw detection data and may include data that is obtained by performing a predetermined process on detection data. For example, the data set may include a feature value extracted from detection data acquired in a certain period. For example, the data set may include a maximum value, a minimum value, a local maximum value, a local minimum value, an average value, etc. of detection data obtained in one practice. The control unit 510 may calculate a feature value from the detection data accumulated in the data accumulation unit 520. Alternatively, feature values may be accumulated in the data accumulation unit 520.

Then, the criterion generation unit 510a reads out (inputs) rehabilitation data that is prepared as described above from the data accumulation unit 520 on a dataset-by-dataset basis (step S1). The rehabilitation data input in the step S1 includes at least the setting parameter, part of the staff data, and part of the index data.

Needless to say, a plurality of types of setting parameters may be included in the rehabilitation data. Further, although the rehabilitation data may include values of all the setting parameters, it may include only values that have been adjusted and thereby changed at that time point. In either case, it is possible to calculate, for example, the time and/or the frequency of changes of each setting parameter. As described above, the staff data is data indicating the training staff member 901 who assists the trainee 900, and may include, for example, a name or an ID of the training staff member 901 and a name of a hospital to which the training staff member 901 belongs. In particular, the staff data used here may include a name or an ID for identifying the training staff member 901. As described above, the index data is data indicating the degree of recovery of the trainee 900, and may include, for example, FIM efficiency of a walking FIM.

Next, the criterion generation unit 510a determines, for each data set, a level indicating an evaluation (e.g., a degree of competence) of the training staff member based on the input rehabilitation data (step S2). It can be considered that the criterion generation unit 510a includes a selection unit that selects a training staff member(s) (e.g., a competent training staff member(s)).

The criterion generation unit 510a can determine the level in accordance with a predetermined level determination criterion for the index data. The predetermined level determination criterion may be to meet at least one of the following conditions (a) to (d) in terms of, for example, FIM efficiency, a walking speed, and stability of walking. However, the level determination criterion is not limited to this example. One of the simplest examples is years of experience. Note that the FIM efficiency is an example of a value indicating the recovery speed of the trainee.

(a) The average value or maximum value of the FIM efficiency (e.g., the length of a period before the FIM reaches six points or higher, or the length of a period before the patient can walk without assistance) for all the trainees assisted by the training staff member of interest is equal to or lower than a threshold.

(b) The average value or minimum value of the walking speed for all the trainees assisted by the training staff member of interest is equal to or higher than a threshold. Alternatively, the rate of increase of the walking speed is equal to or higher than a threshold.

(c) The average value or maximum value of the frequency of occurrences of abnormal walking in level-ground walking (walking on the treadmill 131) for all the trainees assisted by the training staff member of interest is equal to or lower than a threshold. Alternatively, the rate of decrease in the frequency is equal to or higher than a threshold.

(d) The indicator of the beauty of the walking for all the trainees assisted by the training staff member of interest is equal to or higher than a threshold. Note that an index indicating beauty of walking is included in the index data. Alternatively, the rate of increase of this index is equal to or greater than a threshold.

For each of the above-described items (a) to (d), a threshold set consisting of m-1 thresholds for m levels is prepared. Further, the threshold sets of the above-described items (a) to (d) are different from one another. Further, although data for all the trainees assisted by the training staff member of interest are processed by using thresholds in the above-described items (a) to (d), data for all the rehabilitation practices assisted by the training staff member of interest may also be processed by using thresholds. In this way, it is possible to take account of cases where two or more training staff members assist one trainee at the same time or in different periods.

Further, the process using thresholds can also be performed for rehabilitation data in which rehabilitation in which the training staff member takes part as the main staff member is distinguished from rehabilitation in which the training staff member takes part as an assistance staff member. Similarly, the process using thresholds can also be performed for rehabilitation data in which rehabilitation in which the training staff member takes part as a staff member operating the management monitor 139 is distinguished from rehabilitation in which the training staff member takes part as a staff member assisting the trainee (supporting the trainee by hand).

As a simple example, the criterion generation unit 510a may define that the number of levels in each of the above-described items (a) to (d) is two and determine whether or not the training staff member is competent through the process using thresholds. Then, the criterion generation unit 510a may determine that the training staff member is competent (i.e., at a predetermined level or higher) when he/she is determined to be competent for at least three conditions. Further, in a simpler example, the criterion generation unit 510a may use only the above-described item (a) as the condition and define that the number of levels is two. Then, the criterion generation unit 510a may determine a competent staff member, i.e., determine whether or not the training staff member is competent by performing the process using one threshold.

For the above-described determinations, basically, it is necessary to distinguish between training staff members. Therefore, in order to distinguish between training staff members, a name or an ID may be included in the staff data as described above. Note that even when such information is not included in the staff data, it is possible to roughly distinguish training staff members based on other information such as years of experience and an age.

In particular, the level determination unit 510a may determine the above-described level for each feature of the trainee 900. Note that in this case, it is assumed that the rehabilitation data includes trainee data indicating a feature(s) of the trainee 900. Examples of the feature of the trainee 900 include a height, a weight, a gender, a disease, and a symptom. Therefore, the trainee data may include physical information indicating such features. In this way, the level determination unit 510a can classify (i.e., select), for each gender of the trainees 900, training staff members who are considered to be competent for trainees having that gender.

In particular, the trainee data may include symptom data indicating at least one of a disorder (a name of a disease or a disorder) and a symptom of the trainee 900. This is because it is expected that the training staff member may be good at assisting for some diseases and symptoms of the trainee 900, but weak at assisting for other diseases and symptoms thereof. Further, for example, the adjustment value of the setting parameter may also change according to the disease and the symptom of the trainee 900. The symptom data is data in which the above-described symptom information is described. In particular, in the case of walking training, examples of symptoms that are included in the symptom data include a trunk backward movement, a trunk forward bending, a trunk diseased-side movement, a knee joint flexion, difficulty of the toe-off, difficulty in keeping the swinging leg, a trunk backward bending, a pelvic retreat, a lower leg forward bending, a knee joint extension, a flexed knee joint, and swinging. Further, examples of the symptoms that are included in the symptom data include a trunk normal-side movement, vaulting, pelvic elevation, hip joint external rotation, circumduction, and a medial whip. In this way, the level determination unit 510a can classify (i.e., select), for each disease or symptom of the trainees 900, training staff members who are considered to be competent for trainees having that disease of symptom.

Further, the rehabilitation data may also include, in addition to the feature (or as a concept that is included in the feature) of the trainee 900, data indicating a preference(s) of the trainee 900 entered in the walking training device 100. In this way, the criterion generation unit 510*a* may determine the above-described level for each preference of the trainee 900 and classify (i.e., select) a training staff member(s) who is considered to be competent for a trainee having that preference.

Further, the criterion generation unit 510*a* may be configured so as to determine the above-described level for each value indicated by certain index data such as an initial FIM of the trainee 900. In this way, the level determination unit 510*a* can classify (i.e., select), for each value indicated by the index data of the trainees, training staff members who are considered to be competent for trainees having that value.

Then, as a result of the above-described level determination, the criterion generation unit 510*a* extracts rehabilitation data corresponding to the training staff member(s) determined to be at the predetermined level or higher (i.e., the training staff member(s) who is competent to a certain level or higher) (step S3).

Next, the criterion generation unit 510*a* statistically processes the extracted rehabilitation data in regard to the adjusted setting parameter (step S4). This statistical process includes a process for determining the frequency of adjustments (hereinafter also referred to as an adjustment frequency) for each setting parameter. In particular, the statistical process may include a process for determining a frequency of adjustments in which the value is adjusted in an increasing direction and a frequency of adjustments in which the value is adjusted in a decreasing direction. Further, the statistical process may also include a process for determining a frequency of adjustments in which the value is adjusted in a direction in which the level of difficulty of the training is increased and a frequency of adjustments in which the value is adjusted in a direction in which the level of difficulty of the training is decreased.

Each of these statistical processes can be performed without distinguishing the training staff members. However, the statistical process in the step S4 includes a statistical process performed for the setting parameter that is adjusted for each training staff member. The result of this statistical process for each training staff member is accumulated in the data accumulation unit 520 as data about a history of changes (hereinafter referred to as "change history data") or the like of the setting parameter and will be referred to in an operation stage that will be performed later. This change history data may include, for example, information as to whether or not the default value has been changed.

The criterion generation unit 510*a* generates an adjustment criterion for each setting parameter based on the result of the statistical process and stores the generated adjustment criterion in the data accumulation unit 520 so that the determination unit 510*b* can refer to the stored adjustment criterion (step S5). Regarding the adjustment criterion generated in the above-described process, in the step S4, for example, it is possible to generate an average value of adjustment frequencies of a given setting parameter (an average value of frequencies of adjustments performed by a training staff member having a predetermined level or higher because the step S3 has already been performed) as the adjustment criterion of that setting parameter.

Note that the frequency value (number of times) itself may not be used as the frequency. For example, a value of a ratio indicating, out of ten trainees, the number of trainees for whom the setting parameter has been adjusted may be used as the frequency. For example, assume a setting parameter that has been adjusted, by a training staff member having a predetermined level or higher, for two trainees out of ten trainees. In this case, the adjustment criterion may be defined as 20%.

Further, in the step S5, for example, when the level is determined for each feature of the trainee 900, the adjustment criterion for each setting parameter may be generated for each feature. The same applies even when a method for determining a level for an item other than the feature is used. Needless to say, for example, when the level is determined for each of a plurality of items, such as when the level is determined for each feature and for each initial FIM, the adjustment criterion for each setting parameter may be generated for each combination of them.

Further, the criterion generation unit 510*a* also performs a statistical process for rehabilitation data that have not been extracted in the step S3, i.e., rehabilitation data corresponding to training staff members having a level lower than the predetermined level, i.e., performs a statistical process for rehabilitation data for each of the training staff members in regard to the adjusted setting parameter (step S6). The method for this statistical process is the same as that in the step S4. The result of this statistical process is accumulated as change history data or the like of the setting parameter together with the result of the statistical process for each training staff member for the rehabilitation data corresponding to training staff members having the predetermined level or higher in the step S4, and will be referred to in the operation stage that will be performed later. Note that there is no particular limitation on the order of the steps S3 to S5 and the step S6.

(Operation Stage)

Figure 6:
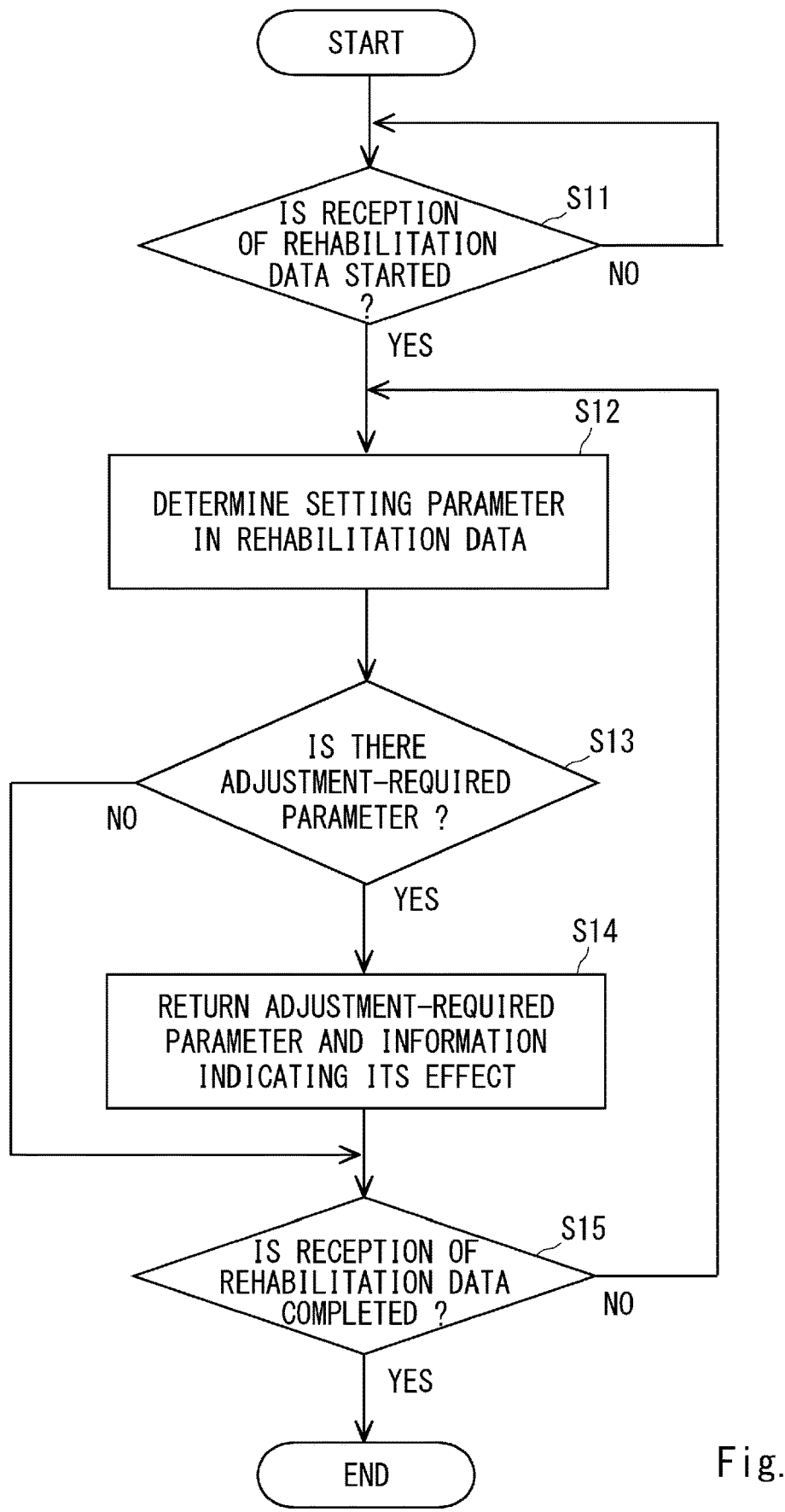
FIG. 6 is a flowchart for explaining an example of determination and output processes performed in the rehabilitation support system shown in FIG. 1.
Figure 7:
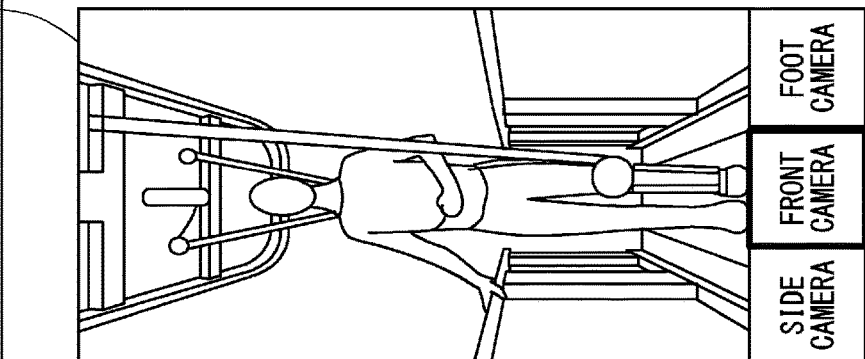
FIG. 7 shows an example of an image shown to a training staff member in the process shown in FIG. 6.

Next, details of the determination process and the outputting process in the rehabilitation support system will be described with reference to FIGS. 6 to 8. FIG. 6 is a flowchart for explaining an example of this process and FIG. 7 shows an example of an image shown to the training staff member 901 in the process shown in FIG. 6. Further, FIG. 8 shows another example of an image shown to the training staff member 901 in the process shown in FIG. 6.

In the operation stage described below, in general, the walking training apparatus 100 and the server 500 connected thereto cooperate with each other. That is, they serve as a rehabilitation support system (a walking training system) and perform a determination process and an outputting process. The above-described output unit exemplified by the response processing unit 510*c* of the server 500 outputs parameter information and effect information to the walking training apparatus 100 side. Further, the walking training apparatus 100 receives these output information pieces and outputs them so that the training staff member 901 can recognize them. In this way, it is possible to educate various training staff members (including training staff members belonging to different hospitals) by using the common server 500 for a plurality of walking training apparatuses. While this process is a process for educating the training staff member 901, it also indirectly corresponds to a process for supporting the trainee 900 so that he/she can carry out rehabilitation more effectively (i.e., a rehabilitation support process).

Firstly, the walking training apparatus 100 outputs rehabilitation data related to rehabilitation performed by the trainee 900 by using the walking training apparatus 100 to the server 500 in order to input the rehabilitation data into the determination unit 510*b* of the server 500. As a configuration for this purpose, the walking training apparatus 100 may include an input/output control unit 210c and an input/output unit 231. In the operation stage, it is desirable that the walking training apparatus 100 output rehabilitation data at least when a setting before the start of training is completed, and also before a rehabilitation practice is performed after a break. However, the walking training apparatus 100 may output rehabilitation data at each time point during the rehabilitation, at the time when a setting parameter is adjusted, at predetermined intervals, and so on. The rehabilitation data transmitted from the walking training apparatus 100 to the server 500 includes a setting parameter(s) as described above.

When the response processing unit 510c of the server 500 receives the rehabilitation data through the communication IF 514 (Yes at step S11), it starts a response process. The response processing unit 510c passes the received data to the determination unit 510b.

The determination unit 510b accumulates the received rehabilitation data in the data accumulation unit 520 and performs a statistical process (including calculation of an adjustment frequency) for each setting parameter included in the rehabilitation data. This statistical process can be performed by using the result of the statistical process obtained in the step S6, which are accumulated in the data accumulation unit 520, for each setting parameter included in the received rehabilitation data. Then, in this statistical process, at least the frequency of adjustments performed by the training staff member 901, including the rehabilitation data received this time, is obtained. Note that since it is necessary to obtain the frequency of adjustments by the training staff member 901 currently assisting the training, the rehabilitation data that is transmitted to the server 500 in the operation stage includes staff data.

Further, the determination unit 510b performs a process for comparing the calculated adjustment frequency with the adjustment criterion and thereby determining whether or not the former is lower than the latter for each setting parameter (step S12). In the step S12, the determination unit 510b determines whether or not each of the input setting parameters is a parameter that needs to be adjusted (a parameter that is desired to be adjusted).

Note that as described above, the adjustment criterion can be generated based on rehabilitation data of a training staff member(s) having a predetermined level or higher. Further, the determination unit 510b determines an adjustment-required parameter based on the adjustment criteria generated as described above. Further, in general, a training staff member having a predetermined level or higher may be regarded as a training staff member whose trainee(s) shows a satisfactory degree of recovery. As described above, it is desirable that the determination unit 510b determine, as the adjustment-required parameter, a setting parameter of which the frequency of adjustments is lower than a frequency with which a training staff member whose trainee(s) shows a satisfactory degree of recovery make adjustments. In this way, it is possible to output, as the adjustment-required parameter, a parameter with which the degree of recovery of a trainee is improved, and thereby to improve the educational effect even further.

Note that, as described above, the adjustment criterion may have a value that is defined for each setting parameter based on the frequency of adjustments by a training staff member(s) having a predetermined level or higher, such as a training staff member(s) whose trainee(s) shows a satisfactory degree of recovery. However, for example, the rehabilitation support system may also be configured in such a manner that the adjustment criterion is unchanged regardless of the setting parameter and a weight is assigned for each setting parameter based on the frequency of adjustments by a training staff member(s) having a predetermined level or higher.

When there is an adjustment-required parameter(s) as a result of the determination in the step S12 (Yes at step S13), the response processing unit 510c reads out effect information that is stored in the data accumulation unit 520 in advance and indicates an adjustment effect that is obtained when that adjustment-required parameter is adjusted. Then, the response processing unit 510c outputs (returns) the effect information together with the parameter information indicating the adjustment-required parameter to the walking training apparatus 100 side through the communication IF 514 (step S14). When there are a plurality of adjustment-required parameters, the response processing unit 510c returns parameter information and effect information for each of the adjustment-required parameters. The information to be returned may be a command to the walking training apparatus 100. If the determination result at the step S13 is No, the response processing unit 510c proceeds to a step S15 (which will be described later) without going through the step S14.

After the process in the step S14, the response processing unit 510c determines whether or not the reception of the rehabilitation data has been completed (step S15). Then, when the reception has been completed, the response processing unit 510c finishes the process, whereas when the reception has not been completed, it determines that the rehabilitation is in progress and returns to the step S12.

The walking training apparatus 100, which has received the command returned from the server 500 in the step S14, outputs these information pieces so that the training staff member 901 can recognize them. Specifically, in the walking training apparatus 100, the input/output control unit 210c receives the command transmitted in the step S14 and passes the received command to the notification control unit 210d. The notification control unit 210d performs notification control corresponding to this command for the display control unit 213 or an audio control unit (not shown).

It is also possible to store notification controls each of which corresponds to a respective one of the commands in the command group that could be transmitted from the server 500 side in the notification control unit 210d in advance. In such a case, the notification control unit 210d makes the display control unit 213 output, to the management monitor 139, a display control signal for displaying, for example, an image corresponding to the command on the management monitor 139. For example, the notification control unit 210d makes the aforementioned audio control unit output, to a speaker(s), an audio control signal for outputting a sound corresponding to the command from the speaker(s). Note that when the received command is a command for reproducing a video content, a video content stored in a storage destination indicated by the command may be reproduced. The storage destination may be in the server 500 as described above, or may be inside the walking training apparatus 100.

In the walking training apparatus 100, for example, a GUI (Graphical User Interface) image 139a shown in FIG. 7 may be displayed on the management monitor 139 based on the command received from the server 500. Note that the GUI image 139a may be superimposed as a pop-up image on an image that is displayed on the management monitor 139 during the rehabilitation.

The GUI image 139a may include a list 139b showing adjustment-required parameters, their adjustment methods (such as directions of adjustments and amounts of adjustments), and their adjustment effects. The list 139*b* includes, for example, information indicating that walking generally becomes easier when the level of swinging assistance is raised. As a simple example, the list 139*b* may include information indicating which setting parameter may be changed in order to alleviate which symptom (e.g., circumduction) that occurs (i.e., is observed) during the training.

As described above, the indicated adjustment effect may be only a short-term adjustment effect such as an effect as to which symptom that occurs during the training is alleviated or what kind of abnormal walking pattern is alleviated. However, the indicated adjustment effect may be a long-term adjustment effect. For example, an adjustment of a setting parameter in a direction in which circumduction is increased often has a high training effect. Therefore, such an adjustment method and its adjustment effect may be shown. Further, the indicated adjustment effect may include both long-term and short-term adjustment effects. In general, the closer the level of training is to the optimum level of difficulty, the greater the training effect (the therapeutic effect) is achieved. Therefore, it is desirable that both long-term and short-term adjustment effects be shown. For example, it is possible to, for a given adjustment-required parameter, indicate that toe-off becomes easier as a short-term effect and indicate a negative effect that it takes time to recover (e.g., to improve the FIM) as a long-term effect. For example, it is possible to, for a given adjustment-required parameter, indicate an effect that circumduction is alleviated and indicate a negative effect that it takes time to recover.

Further, by calculating an average value or an average increase value of the degree of recovery (an FIM, an SIAS, etc.) from the rehabilitation data of the training staff member(s) having the predetermined level or higher in advance at the time when the adjustment criterion is generated, a value that is calculated in such a specific manner can be used as an adjustment effect to be indicated.

Further, the GUI image 139*a* may include a video image 139*c* showing a state of training performed by the trainee 900. Further, this image can be switched depending on which of a side camera selection area 139*d*, a front camera selection area 139*e*, and a foot camera selection area 139*f* is selected. In this way, the training staff member 901 can examine the pros and cons of the adjustment while checking the trainee 900 though the video image.

Further, regarding each of the adjustment-required parameters in the list 139*b*, when its area is selected, a GUI image through which a user can adjust that adjustment-required parameter may be activated. Alternatively, such a GUI image may be displayed as a pop-up image and superimposed on the originally-displayed image. Further, regarding each of the adjustment methods in the list 139*b*, when its area is selected, a GUI image through which a user can make an adjustment according to that method may be activated. Alternatively, such a GUI image may be displayed as a pop-up image and superimposed on the originally-displayed image.

Further, as described above, the criterion generation unit 510*a* can determine, for each symptom of the trainee 900, the level of the training staff member based on the symptom data indicating the symptom of the trainee 900, and generate an adjustment criterion from the rehabilitation data of the training staff member(s) having the predetermined level or higher. In this case, the determination unit 510*b* can also input symptom data indicating the symptom of the trainee 900 who performs the training, and determine, as an adjustment-required parameter, a setting parameter of which the frequency of adjustments is low for that symptom (i.e., for the adjustment criterion generated for that symptom).

In this way, it is possible to determine, as an adjustment-required parameter, a setting parameter that has not been changed according to the symptom (the past symptom and/or the current symptoms) of the trainee 900, and output the determined setting parameter together with its adjustment effect. In reality, even a setting parameter that has not been used has a different weight depending on the symptom of the trainee 900. Therefore, it is possible to enable the training staff member 901 to recognize such a setting parameter. As described above, in this embodiment, by performing a process on a symptom-by-symptom basis, it is possible to output, as an adjustment-required parameter, a setting parameter that is desired to be adjusted while taking the symptom of the trainee 900 into consideration, and thereby to improve the educational effect even further.

Similarly, in the case where an adjustment criterion is generated for each feature of the trainee 900, the determination unit 510*b* inputs trainee data indicating a feature of the trainee 900, and determines, as an adjustment-required parameter, a setting parameter of which the frequency of adjustments is low for the adjustment criterion generated for that feature. The same applies to a process for each disease of the trainee 900, each preference thereof, and each value indicated by certain index data.

As described above, this embodiment can be configured so as to output an adjustment-required parameter and its adjustment effect as a result of a process that is performed according to at least one of the symptom of the trainee 900, the disease thereof, the feature thereof, the preference thereof, the value indicated by certain index data, and so on. In this way, the training staff member 901 can robustly cope with any type of trainee 900.

Further, the determination unit 510*b* determines importance of an adjustment-required parameter, and the response processing unit 510*c* outputs parameter information and effect information according to the determined importance. In this way, it is possible to output the information while changing its outputting method or the like depending on whether or not the adjustment-required parameter is one that is important to improve the training result in the walking training apparatus 100, and thereby to improve the educational effect even further.

For example, a GUI image 139*g* shown in FIG. 8 includes a list 139*h* in which one set of parameter information and effect information is differentiated from the other sets as compared to the list included in the GUI image 139*a*. In this example, information 139*i* including important parameter information and effect information is displayed in a color different from that of the other information. Alternatively, for example, information including important parameter information and effect information may be blinked. As described above, the response processing unit 510*c* can display an important adjustment-required parameter in a different displaying format (e.g., in a different color, a different size, a different font, etc.) from that of the other adjustment-required parameters. Further, the response processing unit 510*c* can output parameter information and effect information only for a predetermined number of adjustment-required parameters, e.g., only for three adjustment-required parameters according to the importance.

Regarding the importance, the determination unit 510*b* can determine, for example, an adjustment-required parameter having a large deviation (a large difference) from its adjustment criterion as an important adjustment-required parameter. Further, the determination unit 510*b* can also determine importance according to the number of cancellations. The cancellation means that although parameter information and effect information were output, their setting parameter was not adjusted (was ignored). In other words, for example, the determination unit 510b can change, according to importance of an adjustment-required parameter, the number of cancellations for preventing its information from being output. However, the process in which the number of cancellations is taken into consideration may be limited to cases where information is output for a training staff member(s) having a predetermined level or higher. This is because the process in which the number of cancellations is taken into consideration could delay education for a training staff member(s) having a level lower than the predetermined level.

Further, in the case where an adjustment criterion is generated for each symptom of the trainee 900, the output unit exemplified by the response processing unit 510c may display an adjustment-required parameter that has not been adjusted in spite of an occurrence of a symptom in a displaying format different from that of the other adjustment-required parameters. In order to enable an adjustment-required parameter to be displayed in the above-described manner, for example, a correspondence relation between symptoms and adjustment-required parameters having strong influences on these symptoms (i.e., adjustment-required parameters important for these symptoms) may be stored in advance in such a state that they can be read by the response processing unit 510c.

Further, the determination unit 510b can also determine whether or not a setting parameter that is associated beforehand with a setting parameter adjusted by the walking training apparatus 100 as a setting parameter that is recommended to be adjusted at the same time as the adjusted parameter is regarded as the adjustment-required parameter. That is, the walking training apparatus 100 can be configured so that when the training staff member 901 adjusts a certain setting parameter, its associated setting parameter (i.e., a setting parameter that mutually interferes with the certain setting parameter) is recommended to be adjusted as an adjustment-required parameter. In particular, each setting parameter may be associated, among those that mutually interfere with that setting parameter, only with one(s) that mutually interferes with that setting parameter to a certain degree or higher. In this way, it is possible to output, as an adjustment-required parameter, a parameter that is desired to be adjusted at the same time as the adjusted parameter, and thereby to improve the educational effect even further.

Further, the walking training device 100 can be configured so that a training mode indicating a training policy can be set. For example, the walking training device 100 can have modes such as a walking speed-oriented mode and a gait-oriented mode in which an appearance is considered to be important as modes corresponding to a long-term training policy. Further, default setting parameters and the like may be changed according to the mode.

In the case where the above-described configuration is adopted, the determination unit 510b can make a determination based on an adjustment criterion that changes according to the training mode. Adopting an adjustment criterion that changes according to the mode for a certain setting parameter means that the weighting of the output (the output for a notification as an adjustment-required parameter) of that setting parameter is changed according to the mode. In this way, it is possible to output, as an adjustment-required parameter, a parameter that is desired to be adjusted according to the training mode, and thereby to improve the educational effect even further. Further, the response processing unit 510c can also be configured so as to output information in an output mode that changes according to the training mode (e.g., in a displaying format that changes according to the training mode). Further, this configuration can be used together with the determination process using different adjustment criteria performed by the determination unit 510b.

The above description is given on the assumption that parameter information and effect information are output to training staff members at all the levels. This is because even a competent training staff member has a setting parameter of which the frequency of adjustments is low and it is necessary to call his/her attention to such a setting parameter.

However, the walking training apparatus 100 can be configured so as to perform the process related to the output of parameter information and effect information only for training staff members 901 having a level lower than the above-described predetermined level. In the casa where staff data is included in the rehabilitation data output from the walking training apparatus 100 to the server 500, the above-described process becomes feasible by storing data indicating the level of each training staff member in the data accumulation unit 520 in advance and referring to the stored data. In this way, it is possible to prevent unnecessary notifications from being provided to training staff members who are assumed to require no notification. In this case, the statistical process for each training staff member in the step S4 shown in FIG. 5 may be skipped. This is because it is possible to determine that training staff members who are not included in the result of the statistical process in the step S6 as training staff members having the predetermined level or higher.

(Effect)

As described above, in this embodiment, it is possible to customize and output adjustment-required parameters and their adjustment effects for each training staff member. Therefore, according to this embodiment, it is possible to educate the training staff member 901, who assists the training, so that he/she can appropriately assist the trainee 900 using the walking training apparatus 100. For example, in this embodiment, it is possible to show the effect of the adjustment of a setting parameter (the effect based on data of a competent PT(s)) as a difference from a training staff member himself/herself who has not adjusted that setting parameter. In this way, according to this embodiment, a training staff member 901 who usually does not adjust a setting parameter can adjust the setting parameter with confidence.

Further, depending on the training staff member 901, there are setting parameters that are adjusted and those that are not adjusted. However, in reality, it is often impossible to appropriately perform training unless many setting parameters are adjusted. However, in this embodiment, since it is possible to show a different adjustment-required parameter(s) and its effect(s) for each training staff member, the above-described problem can be solved.

Further, since training is assisted by the training staff member 901 who has been appropriately educated as described above, variations among training results of training staff members are reduced, thus enabling the trainee 900 to achieve good training results irrespective of which training staff member has assisted the trainee 900. In particular, in this embodiment, such education can be provided in real time during the training.

(Other Education Timings and their Effects)

Further, the processing apparatus according to this embodiment may be the server 500 as described above, and the server 500 may be a server accessible from the terminal apparatus 600. The terminal apparatus 600 may be an apparatus used by the training staff member 901 or provided in the hospital. The terminal apparatus 600 may not be an apparatus that the training staff member 901 usually uses. In such a case, as long as it is an apparatus provided in the hospital, it may be used by the training staff member 901. In this way, the training staff member 901 can check an adjustment-required parameter and its effect information at a desired timing, such as in a time period other than during the training, and thus making it possible to improve the educational effect even further.

Further, the server 500 may be configured so as to output a video content including parameter information and effect information to the terminal apparatus 600. In this way, it is possible to show an adjustment-required parameter and its effect information to a training staff member 901 at a timing desired by that training staff member so that the training staff member 901 can easily understand them. As a result it is possible to improve the educational effect even further. Needless to say, the video content may include a voice of a sound that can be output from the audio output unit.

Further, even in such a case, the video content to be output may be a video image that is obtained by selecting a characteristic part(s) of an actual video image of each trainee (e.g., a part(s) where a certain symptom occurred), or may include such a video image. In particular, by having the training staff member 901 check such a video content possibly with the trainee 900 during a break or immediately after the training, it becomes possible to adjust a setting parameter(s) to a more desirable value(s) in the next practice or in the next training. Further, the server 500 may also be configured so as to attach such a video content or a link to the video content to an email and send the email to an email address of the training staff member who has assisted the training by an email or the like.

(Supplemental Remarks on Method and Program)

As can be understood from the above description, in this embodiment, a processing method including the following determination step and outputting step can also be provided. In the determination step, an adjustment-required parameter(s) is determined from among parameters that can be adjusted in the walking training apparatus 100. The adjustment-required parameter is a parameter of which the frequency of adjustments by a training staff member 901 who assists a trainee 900 performing walking training in the walking training apparatus 100 or by a staff member other than the training staff member 901 in the hospital is lower than an adjustment criterion. In the outputting step, parameter information indicating the adjustment-required parameter and effect information indicating an adjustment effect that is obtained when the adjustment-required parameter is adjusted is output. Further, in this embodiment, as can be understood from the above description, it is also possible to provide a program for causing a computer incorporated in or externally connected to the above-described walking training apparatus 100 to perform the above-described determination step and the outputting step.

Second Embodiment

In the first embodiment, an example in which the server 500 includes the determination unit 510b and the response processing unit 510c, which serves as the output unit, and output control is performed by the server 500 is shown. In contrast, in this embodiment, the determination unit and the output unit are both provided on the walking training apparatus 100 side. A part(s) of the determination unit and the output unit may be formed by, for example, the overall control unit 210 including the input/output control unit 210c and the notification control unit 210d. The remaining functions of the output unit may be formed by the display control unit 213 and the management monitor 139, or by an audio control unit and a speaker(s) (not shown).

As described above, the processing apparatus according to this embodiment is an apparatus incorporated in the walking training apparatus 100. In this way, it is possible to educate, by using the walking training apparatus 100 alone, the training staff member 901 so that he/she can appropriately assist the trainee. Note that the criterion generation unit exemplified by the criterion generation unit 510a may also be disposed in the walking training apparatus 100. In such a case, the criterion generation process and the statistical process of un-extracted rehabilitation data may be performed in the walking training apparatus 100. Further, the walking training apparatus 100 according to this embodiment can also be configured so as to function as a server accessible from the terminal apparatus 600.

Further, although it is not specifically described, the various examples described above in the first embodiment can also be applied to this embodiment and the same effects as those in the first embodiment, except for those related to the distribution of functions, can be achieved.

Third Embodiment

Figure 9:
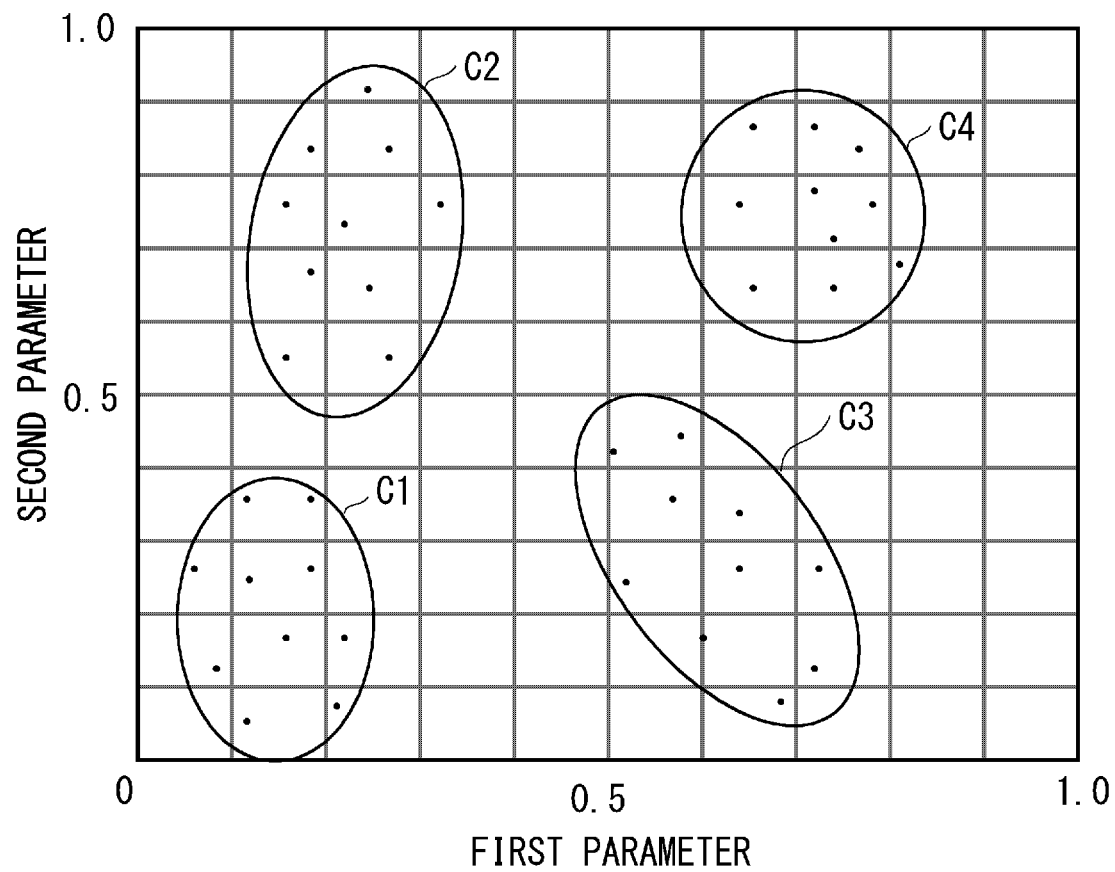
FIG. 9 is a schematic diagram showing an example of a result of a cluster analysis performed in a server in a rehabilitation support system according to a third embodiment.

A third embodiment will be described with reference to FIG. 9. FIG. 9 is a schematic diagram showing an example of a result of a cluster analysis performed by a server in a rehabilitation support system according to the third embodiment. Further, although it is not specifically described, the various examples, including their effects, described above in the first and second embodiments can also be applied to this embodiment, except for the below-described difference.

A processing apparatus according to this embodiment is different from that according to the first embodiment in that the reference generation unit 510a performs the below-described analysis process, instead of performing the level determination process, in the criterion generation stage. Note that since the operation stage is the same as that in the first embodiment, only the criterion generation stage will be described hereinafter.

Firstly, the criterion generation unit 510a of the server 500 reads out rehabilitation data prepared in the same manner as in the first embodiment from the data accumulation unit 520, and performs analysis process on the read rehabilitation data. In particular, it is appropriate to determine whether or not the training staff member is competent, i.e., whether or not the rehabilitation data is one for which a competent training staff member took part based on the recovery index of the trainee. Therefore, it is important to include the index data in the rehabilitation data.

In the analysis process, the training staff members are classified by performing a cluster analysis on the rehabilitation data that has been read as described above. For this cluster analysis, for example, a k-means method can be used. Although the clusters, which are a result of the analysis, become those into which the tendency of the rehabilitation data is classified, they may be adjusted so that they correspond to respective data groups that are classified according to the level of the competence of the training staff members.

For the cluster analysis, an X-means method in which the k-means method is extended and the number of clusters is automatically specified may be used. Further, for the cluster analysis, other various methods such as Gaussian Mixture Models (GMMs) capable of obtaining a probability density distribution and spectral clustering in which clustering is performed while paying attention to connectivity can be used. Note that in the spectral clustering, firstly, data is converted into a graph by using a ε-nearest neighbor method, a k-nearest neighbor (k-NN) method, a complete linkage method, or the like.

For simplifying the explanation, FIG. 9 shows an example of a result of a cluster analysis performed for two parameters (two items) in the rehabilitation data. In the example shown FIG. 9, a cluster analysis is performed on the rehabilitation data while specifying the number of clusters (data groups) as four. As a result, the rehabilitation data is classified into clusters C1 to C4. Note that, in general, the number of parameters of the cluster analysis (the number of spatial axes) can be made equal to the number of items in the rehabilitation data. Therefore, the number of parameters can be set to three or larger in this embodiment.

The criterion generation unit 510a selects, as rehabilitation data used to generate an adjustment criterion, rehabilitation data corresponding to a training staff member included in one of the groups (one of the clusters) into which the training staff members are classified in the analysis process. Note that the statistical process is also performed for the un-selected rehabilitation data as described above in the description of the process for the un-extracted rehabilitation data (step S6) in the first embodiment.

Further, the criterion generation unit 510a generates an adjustment criterion for each setting parameter from the selected rehabilitation data. For example, the criterion generation unit 510a can generate, for a giving setting parameter, an average value in the selected rehabilitation data as its adjustment criterion. Note that the definition of each data and its example in this embodiment are basically the same as those described in the first embodiment. However, the data used in the criterion generation process may be generated from the difference between the level determination process and the analysis process in the criterion generation unit 510a.

Note that the criterion generation unit 510a can use, for each of a plurality of groups into which the training staff members are classified in the analysis process, rehabilitation data corresponding to a training staff member(s) included in that group as rehabilitation data used to generate an adjustment criterion. That is, the criterion generation unit 510a can generate an adjustment criterion for each of the above-described plurality of groups. Further, a coordinator (i.e., a user who makes an adjustment) may select, for example, a group that includes a known competent training staff member(s). Therefore, the server 500 may include a group designation unit that designates the aforementioned group (the cluster). Note that the group designation unit may be configured so as to receive designation of a cluster from an external terminal or the like.

Then, the criterion generation unit 510a generates an adjustment criterion from rehabilitation data corresponding to a training staff member(s) included in the group designated by the group designation unit. In this way, the determination unit 510b can make a determination by using an adjustment criterion that has been obtained by using only the designated group. Then, the coordinator may select an appropriate adjustment criterion, i.e., select appropriate rehabilitation data (an appropriate group), while taking the actually-operated results into consideration, in terms of walking stability, FIM efficiency, walking speed, physical ability, etc. of the trainee.

Fourth Embodiment

The first to third embodiments have been described on the assumption that a notification is provided to a person such as the training staff member 901. However, a notification can also be provided to a non-human training assistant (e.g., a mechanical or artificial training assistant). As the artificial training assistant, there are various types of assistants such as a humanoid robot, a voice assistant program, and a display assistant program. As an example in which a voice assistant program assists the trainee by voice, it is possible to give encouraging talks such as "Please lean your upper body further to the right", "Please hold the handrails", and "Please slow down your walking speed".

When the training assistant is a computer program, it can be incorporated in the walking training apparatus 100 in an executable manner. Alternatively, the program may also be incorporated, in an executable manner, in a portable terminal such as a mobile phone (including a smartphone), a mobile PC, or an external server capable of communicating with the walking training apparatus 100. Further, the artificial training assistant may also include a program with artificial intelligence (an AI program).

Further, a plurality of artificial training assistants may be made available when walking training is performed in the walking training apparatus 100, and each of them may be separately managed in a distinguishable manner. That is, even when the training assistant is an artificial training assistant, the training assistant can be distinguished from other training assistants as in the case of the human training staff member.

Further, when an artificial training assistant is used, examples of the data (the assistant data) related to the artificial training assistant corresponding to the data related to the training staff member 901 in the above-described item (4) include the below-shown data. The examples include functions (such as a voice assist function and an assistance function using a video display) of the artificial training assistant (the program), and a name and a version of the program. Further, when the program is a type of an AI program that learns during its operation, the examples include a learning algorithm, a degree of learning, a learning time, and the number of times of learning.

Further, in the case where a plurality of training assistants (irrespective of whether the assistant is a human assistant or a non-human assistant) simultaneously assist the rehabilitation, the rehabilitation data may include assistant data of the plurality of assistants as in the case of the plurality of human training staff members as described above. Further, each assistant data may also include information indicating whether the assistant is a main training assistant or an assistance training assistant. In addition to or instead of the aforementioned information, each assistant data may include information indicating what kind of assistance is provided.

A notification in this embodiment will be described. For example, when a notification to an artificial training assistant, rather than the human assistant such as the training staff member 901, is required, the notification control unit 210d may notify the artificial training assistant. The notification may be directly provided through communication. Alternatively, the notification may be provided by a video image or a voice as in the case of the human assistant and the video or voice notification may be detected by the artificial training assistant. Further, the artificial training assistant may be configured so as to be able to change the setting or the like of the walking training apparatus 100 through communication or a direct-touching operation. Therefore, it is useful (or meaningful) to educate the artificial training assistant in order to enable it to appropriately assist the trainee.

Alternative Example

Each of the above-described embodiments is described by using an example in which the trainee 900 is a hemiplegic patient who has a disorder in one of his/her legs. However, the walking training apparatus 100 can also be applied to a patient whose legs are both paralyzed. In this case, the patient does training with walking assistance apparatuses 120 attached to both legs. In this case, abnormal walking may be evaluated for each of the diseased legs. The degree of recovery can be individually determined for each diseased leg by independently evaluating abnormal walking for each leg.

Further, although it is not shown in the drawings, the walking training apparatus may be an apparatus that is not equipped with the treadmill 131 of the walking training apparatus 100 shown in FIG. 1, so that the trainee 900 can actually move in the space surrounded by the frame 130. In this case, the frame 130 may be formed so that it has a large length in the traveling direction. Further, it may adopt a configuration in which the harness pulling unit 112, the front pulling unit 135, and the rear pulling unit 137 are moved along guide rails by a motor(s) (not shown) as the trainee 900 moves. Since the trainee 900 actually moves relative to the floor surface, he/she can feel a sense of accomplishment of rehabilitation training more effectively. Needless to say, the walking training apparatus is not limited to these configuration examples.

Further, the level described in each embodiment may be regarded as an example of the degree. In other examples, the degree may be an index value or the like for a value of interest.

Further, although the walking training apparatus 100 has been described as an example to which the present disclosure is applied in each embodiment, the present disclosure is not limited to such examples. That is, the present disclosure may be applied to walking training apparatuses having other configuration, or to other types of rehabilitation support apparatuses other than those for walking training in which rehabilitation performed by trainees is supported or trainees perform training other than the rehabilitation. For example, the rehabilitation support apparatus may be an upper-limb rehabilitation support apparatus that supports rehabilitation of a shoulder(s) or an arm(s). Alternatively, the rehabilitation support apparatus may be a rehabilitation support apparatus that supports rehabilitation for a balancing ability of a trainee. In the case of an apparatus for supporting other types of rehabilitation other than the walking training, the processing apparatus according to each embodiment may be an apparatus that outputs an adjustment-required parameter applied to that apparatus and its adjustment effect. Further, parameters and effects corresponding to the type of rehabilitation or the type of training can be used. Examples of the training other than the rehabilitation include exercises such as walking and running and training. Further, a training support apparatus corresponding to the type of the training can be used. Further, the index data in the case of the training other than the rehabilitation may be data indicating the degree of an improvement in a physical function of the trainee instead of the degree of recovery of the trainee. The degree of an improvement in a physical function may include an improvement in a muscle strength by an exercise or the like and/or an improvement in endurance. Further, even when the training is the rehabilitation, the index data may be data indicating the degree of an improvement in a physical function of the trainee. In this case, the degree of an improvement in a physical function may include the degree of recovery by the rehabilitation or the like. Note that in the case of the training other than the rehabilitation, rehabilitation data may also be referred to as training data.

Further, the processing apparatus described in each embodiment may be formed as a processing system by using a plurality of apparatuses (a plurality of apparatuses over which functions are distributed). For example, at least some of the functions may be incorporated in the server apparatus. For example, the determination process itself performed by the determination unit described in each embodiment may be performed by an apparatus located outside the processing apparatus. In this case, the main body of the processing apparatus includes a result output unit that outputs a determination result, instead of including the determination unit described in each embodiment. Further, a rehabilitation support apparatus described in each embodiment may be formed as a rehabilitation support system by using a plurality of apparatuses. Similarly, the walking training apparatus may be formed as a walking training system by using a plurality of apparatuses, and the training support apparatus may be formed as a training support system by using a plurality of apparatuses. Further, the server (a server system in which server apparatuses or functions are distributed) described in each embodiment may be equipped with only some of the above-described functions. Further, the server described in each embodiment may include at least some of the functions and parts described as the functions and parts of the rehabilitation support apparatus such as the walking training apparatus.

Further, the above-described rehabilitation support apparatus or the server apparatus may have a hardware configuration including, for example, a processor, a memory, and a communication interface. These apparatuses are implemented by making the processor load and execute a program stored in the memory.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A processing system comprising:
a processor programmed to function as:
a criterion generation unit configured to determine an adjustment criterion by accumulating a plurality of data sets within respective predetermined periods, each data set including at least one of raw detection data and data obtained by performing a predetermined process on detection data, each data set being designated with a level indicating an evaluation of a training staff member based on input rehabilitation data, data sets of the plurality of data sets having a designated level above a predetermined level or higher being statistically processed so as to determine the adjustment criterion;
a determination unit configured to determine an adjustment-required parameter, the adjustment-required parameter being, among parameters that are adjustable in a walking training apparatus, a parameter of which a frequency of adjustments by the training staff member, the training staff member being either by a training assistant who assists a trainee performing walking training in the walking training apparatus or an assistant in a hospital other than the training assistant, is lower than the adjustment criterion; and
an output unit configured to output parameter information indicating the adjustment-required parameter and effect information indicating an adjustment effect that is obtained when the adjustment-required parameter is adjusted.

2. The processing system according to claim 1, wherein the determination unit determines, as the adjustment-required parameter, a parameter of which the frequency of adjustments is lower than a frequency with which a training assistant whose trainee shows a satisfactory degree of recovery make adjustments.

3. The processing system according to claim 1, wherein the determination unit determines, as the adjustment-required parameter, a parameter of which the frequency of adjustments is low for a symptom of the trainee.

4. The processing system according to claim 1, wherein the determination unit determines importance of the adjustment-required parameter, and
the output unit outputs the parameter information and the effect information according to the importance of the adjustment-required parameter.

5. The processing system according to claim 1, wherein the determination unit determines whether or not a parameter that is associated beforehand with a parameter adjusted by the walking training apparatus as a parameter that is recommended to be adjusted at the same time as the adjusted parameter is regarded as the adjustment-required parameter.

6. The processing system according to claim 1, wherein
the walking training apparatus is configured so that a training mode indicating a training policy is able to be set, and
the determination unit makes a determination based on the adjustment criterion, the adjustment criterion changing according to the training mode.

7. The processing system according to claim 1, wherein the output unit outputs the parameter information and the effect information to a display device for parameter adjustment incorporated in the walking training apparatus.

8. The processing system according to claim 7, wherein the output unit outputs a video content including the parameter information and the effect information to the display device.

9. The processing system according to claim 1, wherein the processing system is a server system accessible from a terminal apparatus that is used by the training assistant or provided in the hospital.

10. The processing system according to claim 9, wherein the server system outputs a video content comprising the parameter information and the effect information to the terminal apparatus.

11. The processing system according to claim 1, wherein the processing system is an apparatus incorporated in the walking training apparatus.

12. A walking training system comprising:
the processing system according to claim 9; and
a walking training apparatus connected to the processing system, wherein
the output unit outputs the parameter information and the effect information to the walking training apparatus side.

13. A processing method comprising:
a first determination step of determining an adjustment criterion by accumulating a plurality of data sets within respective predetermined periods, each data set including at least one of raw detection data and data obtained by performing a predetermined process on detection data, each data set being designated with a level indicating an evaluation of a training staff member based on input rehabilitation data, data sets of the plurality of data sets having a designated level above a predetermined level or higher being statistically processed so as to determine the adjustment criterion;
a second determination step of determining an adjustment-required parameter, the adjustment-required parameter being, among parameters that are adjustable in a walking training apparatus, a parameter of which a frequency of adjustments by the training staff member, the training staff member being either a training assistant who assists a trainee performing walking training in the walking training apparatus or an assistant in a hospital other than the training assistant, is lower than the adjustment criterion; and
an outputting step of outputting parameter information indicating the adjustment-required parameter and effect information indicating an adjustment effect that is obtained when the adjustment-required parameter is adjusted.

14. A non-transitory computer readable medium storing a program for causing a computer incorporated in or externally connected to a walking training apparatus to perform:
a first determination step of determining an adjustment criterion by accumulating a plurality of data sets within respective predetermined periods, each data set including at least one of raw detection data and data obtained by performing a predetermined process on detection data, each data set being designated with a level indicating an evaluation of a training staff member based on input rehabilitation data, data sets of the plurality of data sets having a designated level above a predetermined level or higher being statistically processed so as to determine the adjustment criterion;
a second determination step of determining an adjustment-required parameter, the adjustment-required parameter being, among parameters that are adjustable in a walking training apparatus, a parameter of which a frequency of adjustments by the training staff member, the training staff member being either a training assistant who assists a trainee performing walking training in the walking training apparatus or an assistant in a hospital other than the training assistant, is lower than the adjustment criterion; and an outputting step of outputting parameter information indicating the adjustment-required parameter and effect information indicating an adjustment effect that is obtained when the adjustment-required parameter is adjusted.

\* \* \* \* \*